(12) United States Patent
Zhang et al.

(10) Patent No.: US 11,214,616 B2
(45) Date of Patent: Jan. 4, 2022

(54) ANTI-TIGIT ANTIBODIES AND THEIR USE AS THERAPEUTICS AND DIAGNOSTICS

(71) Applicant: BEIGENE, LTD., Grand Cayman (KY)

(72) Inventors: Tong Zhang, Beijing (CN); Liu Xue, Beijing (CN); Qi Liu, Beijing (CN); Min Wei, Beijing (CN); Kang Li, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 16/958,262

(22) PCT Filed: Dec. 29, 2018

(86) PCT No.: PCT/CN2018/125375
§ 371 (c)(1),
(2) Date: Jun. 26, 2020

(87) PCT Pub. No.: WO2019/129261
PCT Pub. Date: Jul. 4, 2019

(65) Prior Publication Data
US 2020/0331999 A1    Oct. 22, 2020

(30) Foreign Application Priority Data
Dec. 30, 2017 (WO) ................ PCT/CN2017/120392

(51) Int. Cl.
| C07K 16/00 | (2006.01) |
| A61K 39/00 | (2006.01) |
| C07K 16/28 | (2006.01) |
| A61K 45/06 | (2006.01) |

(52) U.S. Cl.
CPC .......... *C07K 16/2803* (2013.01); *A61K 45/06* (2013.01); *C07K 2317/24* (2013.01); *C07K 2317/54* (2013.01); *C07K 2317/55* (2013.01); *C07K 2317/565* (2013.01); *C07K 2317/622* (2013.01)

(58) Field of Classification Search
CPC ........... C07K 16/2803; C07K 2317/24; C07K 2317/54; C07K 2317/55; C07K 2317/565; C07K 2317/622; A61K 45/06
See application file for complete search history.

(56) References Cited

U.S. PATENT DOCUMENTS

2020/0255516 A1    8/2020    Fu et al.

FOREIGN PATENT DOCUMENTS

| WO | WO 2015/009856 | 1/2015 |
| WO | WO 2016/011264 | 1/2016 |
| WO | WO 2016/028656 | 2/2016 |
| WO | WO 2016/081746 | 5/2016 |
| WO | WO 2017/030823 | 2/2017 |
| WO | WO 2016/106302 | 6/2017 |
| WO | WO 2019/129261 | 7/2019 |

OTHER PUBLICATIONS

International Search Report and Written Opinion for International Application No. PCT/CN2018/125375, dated Mar. 29, 2019, 12 pages.
Beum, P. V. et al., "Loss of CD20 and Bound CD20 Antibody from Opsonized B Gells Occurs More Rapidly Because of Trogocytosis Mediated by Fc Receptor-Expressing Effector Celis Than Direct Internalization by the B Cells," The Journal of Immunology, 2011:187:3438-3447; Prepublished online Aug. 2011.
Boles, K. S. et al., "A novel molecular interaction for the adhesion of follicular CD4 T cells to follicular DC," Eur. J. Immunol., 2009, 39:695-703.
Bottino, C. et al., "Identification of PVR (CD155) and Nectin-2 (CD112) as Cell Surface Ligands for the Human DNAM-1 (CD226) Activating Molecule," J. Exp. Med., vol. 198, No. 4, Aug. 2003, pp. 557-567.
Carlsten, M. et al., "Checkpoint Inhibition of KIR2D with the Monoclonal Antibody IPH2101 Induces Contraction and Hyporesponsiveness of NK Cells in Patients with Myeloma," Clin Cancer Res., Jun. 2016, 22(21):5211-5222.
Casado, J. G. et al., "Expression of adhesion molecules and ligands for activating and costimulatory receptors involved in cell-mediated cytotoxicity in a large panel of human melanoma cell lines," Cancer Immunol Immunother (2009) 58:1517-1526.
Chan, C. J. et al., "The receptors CD96 and CD226 oppose each other in the regulation of natural killer cell functions," Nature Immunology, May 2014, vol. 15, No. 5, pp. 431-438.
Chauvin, J-M et al., "TIGIT and PD-1 impair tumor antigen-specific CD8+ T cells in melanoma patients," Clin Invest. 2015;125(5):2046-2058.
Chew, G. M. et al., "TIGIT Marks Exhausted T Cells, Correlates with Disease Progression, and Serves as a Target for Immune Restoration in HIV and SIV Infection," PLoS Pathog., Jan. 2016, 12(1):e1005349. doi: 10.1371/journal.ppat. 1005349.
Chothia, C. et al., "Canonical structures for the hypervariable regions of immunoglobulins," J. Mol. Biol., Aug. 1987, 196(4):901-917.
Chothia, C. et al., "Conformations of immunoglobulin hypervariable regions," Nature, 342:878-883 (1989).
De St. Groth, S. F. et al., "Production of monoclonal antibodies: strategy and tactics," Journal of Immunological Methods, 35:1-21 (1980).
Engels, N. et al., "The signaling tool box for tyrosine-based costimulation of lymphocytes," Current Opinion in Immunology, 2011, 23:324-329.
Ganesan, L. P. et al., "FcγRIIb on liver sinusoidal endothelium clears small immune complexes," The Journal of Immunology, 2012, 189:4981-4988; Prepublished online Oct. 2012.
Gil Del Alcazar, C. R. et al., "Immune escape in breast cancer during in situ to invasive carcinoma transition," Cancer Discov., 2017, 7(10):1098-1115.

(Continued)

*Primary Examiner* — Lei Yao
(74) *Attorney, Agent, or Firm* — Cooley LLP

(57) ABSTRACT

Provided are antibodies that specifically bind to TIGIT (T cell immunoreceptor with Ig and ITIM domains, WUCAM or Vstm3) and inhibit Tigit-mediated cellular signaling and activities in immune cells. The anti-TIGIT antibodies can be used to treat or diagnose cancer, infectious diseases or other pathological disorders that may be modulated by Tigit-mediated functions.

11 Claims, 7 Drawing Sheets

Specification includes a Sequence Listing.

(56) References Cited

OTHER PUBLICATIONS

Johnston, R. J. et al., "The immunoreceptor TIGIT Regulates Antitumor and Antiviral CD8+ T Cell Effector Function," Cancer Cell, Dec. 2014, 25:923-937.
Joller, N. et al., "Cutting edge: TIGIT has T cell-intrinsic inhibitory functions," Journal of Immunology, 2011; 186:1338-1342.
Joller, N. et al., "Treg Cells Expressing the Coinhibitory Molecule TIGIT Selectively Inhibit Proinflammatory Th1 and Th17 Cell Responses," Immunity, Apr. 2014, 40:559-581.
Kabat, E. A., "The structural basis of antibody complementarity," Adv. Prot. Chem., 32:1-75 (1978).
Kabat, E. A. et al., "Unusual distributions of amino acids in complementarity-determining (hypervariable) segments of heavy and light chains of immunoglobulins and their possible roles in specificity of antibodycombining sites," The Journal of Biological Chemistry, Oct. 1977, vol. 252, No. 19, pp. 5609-6615.
Kabat, E. A. et al., "Sequences of Proteins of Immunological Interest," vol. 1, Fifth Edition, U.S. Department of Health and Human Services, Public Health Service National Institutes of Health (1991), 152 pages.
Kong, Y. et al., "T-Cell Immunoglobulin and ITIM Domain (TIGIT) Associates with CD8ρ T-Cell Exhaustion and Poor Clinica Outcome in AML Patients," Clin. Cancer Res., 2016, 22(12):3057-3066. Published Online Jan. 2016.
Kurtulus, S. et al., "TIGIT predominantly regulates the immune response via regulatory T cells," J Clin Invest. 2015;125(11):4053-4062. https://doi.org/10.1172/JCI81187.
Lefranc, M-P et al., "IMGT, the International ImMumoGeneTics database," Nucleic Acids Research, 27(1):209-212 (1999).
Levin, S. D. et al., "Vstm3 is a member of the CD28 family and an important modulator of T-cell function," Eur. J. Immunol., 2011, 41:902-915.
Li, M. et al., "T-cell Immunoglobulin and ITIM Domain (TIGIT) Receptor/Pollovirus Receptor (PVR) Ligand Engagement Suppresses Interferon-γProductlon of Natural Killer Cells via β-Arrestin 2-mediated Negative Signaling," The Journal of Biological Chemistry, vol. 289, No. 25, Jun. 2014, pp. 17647-17657.
Liu, S. et al., "Recruitment of Grb2 and SHIP1 by the ITT-like motif of TIGIT suppresses granule polarization and cytotoxicity of NK cells," Cell Death and Differentiation (2013) 20:456-464. Published online Nov. 2012.
Mechetner, E., "Development and Characterization of Mouse Hybridomas," Chapter 1 In: Methods in Molecular Biology, vol. 378: Monoclonal Antibodies: Methods and Protocols, Edited by: M. Albitar, Humana Press Inc., Totowa, NJ (2007), 13 pages.
Mendelsohn, C. L. et al., "Cellular receptor for poliovirus: Molecular cloning, nucleotide sequence, and expression of a new member of the immunoglobulin superfamily," Cell, vol. 56, pp. 855-865, Mar. 1939.
Stanietsky, N. et al., "The interaction of TIGIT with PVR and PVRL2 inhibits human NK cell cytotoxicity," PNAS, Oct. 2009, vol. 106, No. 42, pp. 17858-17303.
Stengel, K. F. et al., "Structure of TIGIT immunoreceptor bound to poliovirus receptor reveals a cell-cell adhesion and signaling mechanism that requires cis-trans receptor clustering," PNAS, Apr. 2012, vol. 109, No. 14, pp. 5399-5404.
Tassi, E. et al., "Early Effector T Lymphocytes Coexpress Multiple Inhibitory Receptors in Primary Non-Small Cell Lung Cancer," Cancer Research, 2017, 77(4):851-861. Published online: Dec. 2016.
Taylor, R. P. et al., "Fcγ-receplor-mediated trogocytosis impacts mAb-based therapies: historical precedence and recent developments," Blood, Jan. 2015;125(5):762-766.
Wang, F. et al., "TIGIT expression levels on human NK cells correlate with functional heterogeneity among healthy individuals," Eur. J. Immunology., 2015, 45:2886-2897.
Wu, T. T. et al., "An analysis of the sequences of the variable regions of bence jones proteins and myeloma light chains and their implications for anti-body complementarity," J. Exp. Med., 132(2):211-250 (Aug. 1970).
Xie, J. et al., "Expression of immune checkpoints in T cells of esophageal cancer patients," Oncotarget, vol. 7, No. 39, Aug. 2016, pp. 63669-63678.
Yu, X. et al., "The surface protein TIGIT suppresses T cell activation by promoting the generation of mature immunoregulatory dendritic cells," Nature Immunology, Jan. 2009, vol. 10, No. 1, pp. 48-57.

ANTI-TIGIT ANTIBODIES AND THEIR USE AS THERAPEUTICS AND DIAGNOSTICS

CROSS-REFERENCE TO RELATED APPLICATIONS

This application is a U.S. National Stage Application under 35 U.S.C. § 371 of International Application No. PCT/CN2018/125375, filed Dec. 29, 2018, which claims the benefit of priority to International patent application number PCT/CN2017/120392, filed on Dec. 30, 2017, the disclosures of which are incorporated herein by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BEIG_033_01US_SeqList_ST25.txt, date recorded Jun. 26, 2020, file size 19.1 kilobytes).

FIELD OF THE INVENTION

The present application relates to antibodies that specifically bind to TIGIT (T cell immunoreceptor with Ig and ITIM domains) and uses of the same.

BACKGROUND OF THE INVENTION

Tigit (T cell immunoglobulin and ITIM domain) is a type I transmembrane protein, a member of the CD28 family of proteins that plays an important role in inhibiting T- and NK cell-mediated functional activities in anti-tumor immunity [Boles K S, et al., 2009 *Eur J Immunol,* 39:695-703; Stanietsky N, et al., 2009 *PNAS* 106:17858-63; Yu X, et al. 2009 *Nat. Immunol,* 10:48-57].

The genes and cDNAs coding for TIGIT were cloned and characterized in mouse and human. Full length human TIGIT has a sequence of 244 amino acids (SEQ ID NO: 1) in length, in which the first 21 amino acids consist a signal peptide. The amino acid sequence of the mature human TIGIT contains 223 amino acid (aa) residues (NCBI accession number: NM_173799). The extracellular domain (ECD) of mature human TIGIT consists of 120 amino acid residues (SEQ ID NO: 2, corresponding to amino acids 22-141 of SEQ ID NO: 1) with a V-type Ig-like domain (corresponding to amino acids 39-127 of SEQ ID NO: 1), followed by a 21 aa transmembrane sequence, and an 82 aa cytoplasmic domain with an immunoreceptor tyrosine-based inhibitory motif (ITIM) [Yu X, et al. 2009 *Nat. Immunol,* 10:48-57; Stengel K F et al. 2012 *PNAS* 109:5399-04]. Within the ECD, human TIGIT shares only 59% and 87% aa sequence identity with mouse and cynomolgus monkey, respectively.

TIGIT is expressed on T cells (including activated T cells, memory T cells, regulatory T (Treg) cells, and follicular T helper (Th) cells), and NK cells [Boles K S, et al., 2009 *Eur J Immunol,* 39:695-703; Joller N, et al., 2014 *Immunity* 40:569-81; Levin S D, et al., 2011 *Eur J Immunol,* 41:902-15; Stanietsky N, et al., 2009 *PNAS* 106:17858-63; Yu X et al. 2009 *Nat. Immunol,* 10:48-57].

So far, two Tigit ligands, CD155 (also known as poliovirus receptor or PVR) and CDll2 (also known as poliovirus receptor-related 2, PVRL2, nectin-2), have been identified. These ligands are primarily expressed on APCs (such as dendritic cells and macrophages) and tumor cells [Casado J G, et al., 2009 *Cancer Immunol Immunother* 58:1517-26; Levin S D, et al., 2011 *Eur J Immunol,* 41:902-15; Mendelsohn C L et al., 1989 56:855-65; Stanietsky N, et al., 2009 *PNAS* 106:17858-63; Yu X et al. 2009 *Nat. Immunol,* 10:48-57]. As an immune "checkpoint" molecule, Tigit initiates inhibitory signaling in immune cells when engaged by its ligands, CD155 and CD112. The binding affinity of Tigit to CD155 (Kd: ~1 nM) is much higher than to CD112 and whether the TIGIT: CD112 interaction is functionally relevant in mediating inhibitory signals yet remain to be determined. A co-stimulatory receptor, CD226 (DNAM-1), binds to the same ligands with lower affinity (Kd:~100 nM), but delivers a positive signal [Bottino C, et al., 2003 *J Exp Med* 198:557-67]. In addition, CD96 (Tactile), a "Tigit-like" receptor, also plays a similarly inhibitory role in the same pathway [Chan C J, et al., 2014 *Nat. Immunol* 15:431-8].

Tigit can inhibit immune responses through different mechanisms. First, interaction between TIGIT and PVR on dendritic cells (DCs) could deliver a "reverse signaling" in DCs, leading to up-regulation of IL-10 and decrease of IL-12 secretion, thereby inhibiting T-cell activation [Yu X, et al. *Nat Immunol.* 2009 10:48-57]. Second. TIGIT binds to CD155 with higher affinity, thereby competing off DNAM-1-CD155 interaction. Third, direct ligation of TIGIT on T cells could down-regulate TCR-mediated activation and subsequent proliferation and engagement of TIGIT on NK cells block NK cell cytotoxicity [Joller N, et al. 2011 186: 1338-42; Stanietsky N. et al., 2009 *PNAS* 106:17858-63]. Fourth, Tigit expression on Tregs has been associated with a highly activated and suppressive phenotype in tumor tissue and TIGIT signaling in Tregs may favor Treg stability [Joller N. et al. *Immunity* 2014 40:569-81; Kurtulus S, et al. *J Clin Invest.* 2015125: 4053-4062].

TIGIT has an immunoglobulin tail tyrosine (ITT)-like motif followed by an immunoreceptor tyrosine-based inhibition motif (ITIM) in its cytoplasmic tail [Yu X, et al. *Nat Immunol.* 2009 10:48-57; Engels N, et al. *Curr Opin Immunol* 2011 23: 324-329]. These motifs could mediate recruitment of the phosphatase SHIP-1 and β-arrestin 2 [Li M, et al. *J Biol Chem.* 2014 289:17647-17657; Liu S, et al. *Cell death and differentiation* 2013 20: 456-464], thus providing a mechanism by which TIGIT can intrinsically deliver inhibitory signals to dampen activating signals.

Up-regulation of Tigit expression in tumor-infiltrating lymphocytes (TILs) and peripheral blood mononuclear cells (PBMCs) has been reported in many types of cancers such as lung [Tassi, et al., *Cancer Res.* 2017 77: 851-861], esophageal [Xie J, et al., *Oncotarget* 2016 7.63669-63678], breast [Gil Del Alcazar C R, et al. 2017 *Cancer Discov.*], acute myeloid leukemia (AML) [Kong Y et al., *Clin Cancer Res.* 2016 22:3057-66] and melanoma [Chauvin J M, et al., *J Clin Invest.* 2015 125:2046-2058]. The increased expression of Tigit in AML is associated with poor prognosis of patient survival outcome [Kong Y et al., *Clin Cancer Res.* 2016 22:3057-66]. Not only does up-regulation of Tigit signaling play important roles in immune tolerance to cancer, but also to chronic viral infection. During HIV infection, expression of Tigit on T cells was significantly higher and positively correlated with viral loads and disease progression [Chew G M, et al., 2016 *PLoS Pathog.* 12:e1005349]. In addition, blockade of Tigit receptor alone or in combination with other blockade could rescue functionally "exhausted" T cells both in vitro and in vivo [Chauvin J M, et al., *J Clin Invest.* 2015125:2046-2058; Chew G M, et al., 2016 *PLoS Pathog.* 12:e1005349; Johnston R J, et al. *Cancer Cell* 2014 26:923-937]. In the cases of cancer and viral infections, activation of Tigit signaling promotes immune cell dysfunction, leading to the cancer outgrowth or extended viral infection. Inhibition of Tigit-mediated inhibitory signaling by therapeutic agents may restore the functional activities of immune cells including T cells, NK cells and dendritic cells (DCs), therefore enhancing immunity against cancer or chronic viral infection.

Therefore, modulation of Tigit signaling by antagonistic molecules may rescue immune cells from tolerance, inducing efficient immune responses to eradicate tumors or chronic viral infections.

SUMMARY OF THE INVENTION

The present invention is at least in part based on the discovery of a set of monoclonal antibodies (mAbs) which inhibit Tigit-mediated cellular signaling in immune cells, re-activate the immune cells and enhance immunity by specifically binding to Tigit. Accordingly, in the first aspect, the present application relates to an anti-Tigit antibody and antigen-binding fragment thereof which is capable of binding to human Tigit (SEQ ID NO: 1). The present invention also relates to the humanized version of the anti-Tigit mAbs of the first aspect.

In particular embodiments, the antibody of the present application comprises a heavy chain variable region (VH) comprising one, two or three CDRs having an amino acid sequence selected from SEQ ID NOs: 3, 4, 5 or 13, or variants thereof comprising one or more conservative substitutions, e.g. one or two conservative substitutions in the amino acid sequences of SEQ ID NOs 3, 4, 5 or 13; and/or a light chain variable region (VL) comprising one, two or three CDRs having an amino acid sequence selected from SEQ ID NOs: 6, 7, or 8, or variants thereof comprising one or more conservative substitutions, e.g. one or two conservative substitutions in the amino acid sequences of SEQ ID NOs: 6, 7, or 8.

In a more specific embodiment, the antibody of the present application comprises a heavy chain variable region (VH) comprising a VH-CDR1 having an amino acid sequence of SEQ ID NO: 3 or a variant thereof comprising one or more conservative substitutions, e.g. one or two conservative substitutions, a VH-CDR2 having an amino acid sequence of SEQ ID NO: 4 or SEQ ID NO: 13 or a variant thereof comprising one or more conservative substitutions, e.g. one or two conservative substitutions, and a VH-CDR3 having an amino acid sequence of SEQ ID NO: 5 or a variant thereof comprising one or more conservative substitutions, e.g. one or two conservative substitutions; and/or a light chain variable region (VL) comprising a VL-CDR1 having an amino acid sequence of SEQ ID NO: 6 or a variant thereof comprising one or more conservative substitutions, e.g. one or two conservative substitutions, a VL-CDR2 having an amino acid sequence of SEQ ID NO: 7 or a variant thereof comprising one or more conservative substitutions, e.g. one or two conservative substitutions, and a VL-CDR3 having an amino acid sequence of SEQ ID NO: 8 or a variant thereof comprising one or more conservative substitutions, e.g. one or two conservative substitutions.

The antibody or the antigen-binding fragment thereof of the present application is capable of binding to human Tigit and comprises a heavy chain variable region having an amino acid sequence selected from SEQ ID NO: 9, 14, 19, or a sequence having at least 85%, at least 90%, at least 95%, at least 96%, at least 97%, at least 98%, at least 99% sequence identity with SEQ ID NO: 9, 14, 19. In one embodiment, the difference in sequence lies in the framework region. In one embodiment, the antibody or the antigen-binding fragment thereof comprises a heavy chain variable region encoded by an nucleotide sequence selected from SEQ ID NO: 10, 15 or 20, or a variant thereof.

The antibody or the antigen-binding fragment thereof of the present application is capable of binding to human Tigit and comprises a heavy chain variable region having an amino acid sequence selected from SEQ ID NO: 11, 16, 21, or 24, or a sequence having at least 85%, at least 90%, at least 95%, at least 96%, at least 97%, at least 98%, at least 99% sequence identity with SEQ ID NO: 11, 16, 21 or 24. In one embodiment, the difference in sequence lies in the framework region. In one embodiment, the antibody or the antigen-binding fragment thereof comprising a heavy chain variable region encoded by an nucleotide sequence selected from SEQ ID NO: 12, 17 or 22, or a variant thereof.

In one embodiment, the antibody or antigen-binding fragment thereof is capable of binding to human Tigit with a Kd value of about $1\times10^{-9}$ M to about $1\times10^{-12}$ M. For example, the antibody or the antigen-binding fragment thereof is capable of binding to human Tigit with a Kd value less than about $1\times10^{-9}$ M, less than about $1\times10^{-10}$ M, less than about $1\times10^{-11}$ M, or less than about $1\times10^{-12}$ M.

In one embodiment, the antibody or the antigen-binding fragment thereof comprises a heavy chain constant region of the subclass of IgG1, IgG2, IgG3, or IgG4 or a variant thereof, and a light chain constant region of the type of kappa or lambda or a variant thereof. In a more specific embodiment, the Fc region of the antibody is human IgG1 Fc or a variant thereof, e.g. a Fc region of SEQ ID NO: 18.

In one embodiment, the antibody or antigen-binding fragment thereof promotes the production of IFN-γ by antigen-specific T cells. In a more specific embodiment, the antibody or antigen-binding fragment thereof promotes the production of IFN-γ by antigen-specific T cells in a dose-dependent manner.

In a more specific embodiment, the antibody of the present application reduces the surface expression of Tigit receptor via FcγR-mediated trogocytosis, particularly FcγRIIB-mediated trogocytosis.

In one embodiment, the antibody of the present application shows a pH-dependent antigen binding such that the antibody exhibits a stronger binding to human TIGIT at a mild acidic pH in tumor microenvironment (e.g. pH 6.0) as compared to the binding to human TIGIT at a physiologic pH (e.g. pH 7.4). In a more specific embodiment, the antibody of the present application has (1) a $K_D$ ratio at pH 7.4/pH 6.0 of greater than 2, 3, 4, 5, 6, 7, 8, 9, 10, 20, 30, 40, 50, 60, 70, 80, 90, 100, or more, and/or (2) a Rmax (RU) value at pH 6.0 which is at least 2-fold, 3-fold, 4-fold, 5-fold, 6-fold, 7-fold, 8-fold, 9-fold, 10-fold, 20-fold, 30-fold, 40-fold, 50-fold higher than the Rmax at pH 7.4, as measured by surface plasmon resonance (Biacore) or similar technology.

The anti-Tigit mAbs disclosed herein have potential therapeutic uses in treating cancer, controlling viral infections and other human diseases that are mechanistically involved in immune tolerance or "exhaustion". Accordingly, in further embodiments, the anti-Tigit antibody of the present application is for use in treatment of cancer. In another specific embodiment, the anti-Tigit antibody of the present application is for use in treating an infection, treating an infectious disease and/or controlling viral infections. In another specific embodiment, the anti-Tigit antibody of the present application is for use in the treatment of other human diseases related to or caused by immune tolerance, or the treatment of a disease that can be improved by increasing immune cell activation.

In a further aspect, the present application relates to a composition comprising the anti-Tigit antibody or antigen-binding fragment thereof and a therapeutically acceptable excipient.

DETAIL DESCRIPTION OF THE INVENTION

Definitions

Figure 1:
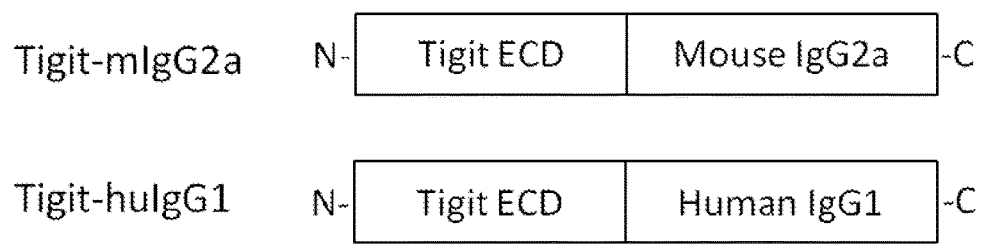
FIG. 1 Schematic diagram of Tigit-mIgG2a (top) and Tigit-huIgG1 (bottom). Tigit ECD: tigit extracellular domain. N: N-terminus. C: C-terminus.

Conservative amino acid substitutions of amino acids are commonly known in the art and exemplarily shown in the table below. Generally, a conservative amino acid substitution means that an amino acid residue is replaced by another amino acid residue having a similar side chain.

| Original amino acid residue | One-letter and three-letter codes | Conservative substitution(s) |
|---|---|---|
| Alanine | A or Ala | Gly; Ser |
| Arginine | R or Arg | Lys; His |
| Asparagine | N or Asn | Gln; His |
| Aspartic acid | D or Asp | Gln; Asn |
| Cysteine | C or Cys | Ser; Ala |
| Glutamine | Q or Gln | Asn |
| Glutamic acid | E or Glu | Asp; Gln |
| Glycine | G or Gly | Ala |
| Histidine | H or His | Asn; Gln |
| Isoleucine | I or Ile | Leu; Val |
| Leucine | L or Leu | Ile; val |
| Lysine | K or Lys | Arg; His |
| Methionine | M or Met | Leu; Ile; Tyr |
| Phenylalanine | F or Phe | Tyr; Met; Len |
| Proline | P or Pro | Ala |
| Serine | S or Ser | Thr |
| Threonine | T or Thr | Ser |
| Tryptophan | W or Trp | Tyr; Phe |
| Tyrosine | Y or Tyr | Trp; Phe |
| Valine | V or Val | Ile; Leu |

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

Throughout this specification and the claims which follow, unless the context requires otherwise, the word "comprise", and variations such as "comprises" and "comprising", will be understood to imply the inclusion of a stated amino acid sequence, DNA sequence, step or group thereof, but not the exclusion of any other amino acid sequence, DNA sequence, step. When used herein the term "comprising" can be substituted with the term "containing", "including" or sometimes "having".

The term "Tigit" includes various mammalian isoforms, e.g., human Tigit, orthologs of human Tigit, and analogs comprising at least one epitope within Tigit. The amino acid sequence of Tigit, e.g., human Tigit, and the nucleotide sequence encoding the same, is known in the art.

The terms "administration", "administering", "treating" and "treatment" as used herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" or "treatment" also includes in vitro and ex vivo treatments, e.g., of a cell, by a reagent, diagnostic, binding compound, or by another cell. The term "subject" herein refers to any organism, preferably an animal, more preferably a mammal (e.g., rat, mouse, dog, cat, rabbit) and most preferably a human.

Antibody or Antibody Molecule

Disclosed herein are antibody molecules that bind to Tigit with high affinity and specificity.

In some embodiments, the anti-Tigit antibody binds to human Tigit and includes at least one, two, three, four, five or six complementarity determining regions (CDR's) comprising an amino acid sequence SEQ ID NOs 3, 4, 5, 13 and SEQ ID NOs: 6, 7, 8. In particular embodiments, the antibody of the present application comprises a heavy chain variable region (VH) comprising one, two or three CDRs having an amino acid sequence selected from SEQ ID NOs: 3, 4, 5 or 13, or a variant thereof comprising one or more conservative substitutions; and/or a light chain variable region (VL) comprising one, two or three CDRs having an amino acid sequence selected from SEQ ID NOs: 6, 7, or 8, or a variant thereof comprising one or more conservative substitutions.

In some embodiments, the anti-Tigit antibody is an isolated antibody, a humanized antibody, a chimeric antibody or a recombinant antibody.

In some embodiments, the anti-Tigit antibody comprises at least one antigen-binding site, or at least a variable region. In some embodiments, the anti-Tigit antibody comprises an antigen-binding fragment derived from an antibody described herein.

The term "antibody" herein is used in the broadest sense and specifically covers antibodies (including full length monoclonal antibodies) and antibody fragments so long as they recognize antigen, e.g., Tigit. An antibody is usually monospecific, but may also be described as idiospecific, heterospecific, or polyspecific. Antibody molecules bind by means of specific binding sites to specific antigenic determinants or epitopes on antigens.

The term "monoclonal antibody" or "mAb" or "Mab" herein means a population of substantially homogeneous antibodies, i.e., the antibody molecules comprised in the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their complementarity determining regions (CDRs), which are often specific for different epitopes. The modifier "monoclonal" indicates the character of the antibody as being obtained from a substantially homogeneous population of antibodies, and is not to be construed as requiring production of the antibody by any particular method. Monoclonal antibodies (mAbs) may be obtained by methods known to those skilled in the art. See, for example Kohler G et al., *Nature* 1975 256:495-497; U.S. Pat. No. 4,376,110; Ausubel F M et al., CURRENT PROTOCOLS IN MOLECULAR BIOLOGY 1992; Harlow E et al., ANTIBODIES: A LABORATORY MANUAL, Cold spring Harbor Laboratory 1988; and Colligan J E et al., CURRENT PROTOCOLS IN IMMUNOLOGY 1993. The mAbs disclosed herein may be of any immunoglobulin class including IgG, IgM, IgD, IgE, IgA, and any subclass thereof. A hybridoma producing a mAb may be cultivated in vitro or in vivo. High titers of mAbs can be obtained by in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as α, δ, ε, γ, or μ, and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (VL/VH) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)", which are located between relatively conserved framework regions (FR). The CDRs are usually aligned by the framework regions, enabling binding to a specific epitope. In general, from N-terminal to C-terminal, both light and heavy chain variable domains sequentially comprise FR-1 (or FR1), CDR-1 (or CDR1), FR-2 (FR2), CDR-2 (CDR2), FR-3 (or FR3), CDR-3 (CDR3), and FR-4 (or FR4). The assignment of amino acids to each domain is, generally, in accordance with the definitions of Sequences of Proteins of Immunological Interest, Kabat, et al., National Institutes of Health, Bethesda, Md.; 5<m> ed.; NIH Publ. No. 91-3242 (1991); Kabat (1978) *Adv. Prot. Chem.* 32: 1-75; Kabat, et al., (1977) *J. Biol. Chem.* 252:6609-6616; Chothia, et al, (1987) *J Mol. Biol.* 196:901-917 or Chothia, et al, (1989) *Nature* 342:878-883.

The term "hypervariable region" means the amino acid residues of an antibody that are responsible for antigen-binding. The hypervariable region comprises amino acid residues from a "CDR" (i.e., VL-CDR1, VL-CDR2 and VL-CDR3 in the light chain variable domain and VH-CDR1, VH-CDR2 and VH-CDR3 in the heavy chain variable domain). See, Kabat et al. (1991) *Sequences of Proteins of Immunological Interest*, 5th Ed. Public Health Service. *National Institutes of Health, Bethesda, Md.* (defining the CDR regions of an antibody by sequence); see also Chothia and Lesk (1987) *J. Mol. Biol.* 196: 901-917 (defining the CDR regions of an antibody by structure). The term "framework" or "FR" residues mean those variable domain residues other than the hypervariable region residues defined herein as CDR residues.

Unless otherwise indicated, "antibody fragment" or "antigen-binding fragment" means antigen binding fragments of antibodies, i.e. antibody fragments that retain the ability to bind specifically to the antigen bound by the full-length antibody, e.g. fragments that retain one or more CDR regions. Examples of antigen binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

An antibody that binds to a specified target protein with specificity is also described as specifically binding to a specified target protein. This means the antibody exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies or binding fragments thereof, useful in the present invention will bind to the target protein with an affinity that is at least two fold greater, preferably at least 10-times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a mature human Tigit molecule, if it binds to polypeptides comprising that sequence but does not bind to proteins lacking that sequence.

The expressions "pH-dependent binding", "pH-dependent target binding" and "pH-dependent antigen binding" are interchangeable in the present disclosure, indicating that the antibody of the present application binds to its target/antigen, namely human TIGIT, in a pH-dependent manner. Specifically, the antibody of the present application shows a higher binding affinity and/or binding signal to its antigen at a mild acidic pH, e.g. pH 6.0, which is usually found in tumor microenvironment, as compared to the binding affinity and/or binding signal at physiologic pH, e.g. pH 7.4. The methods for determining the binding affinity and/or the intensity of binding signal of the antibody of the present application are well known in the art and include but not limited to surface plasmon resonance (Biacore) or similar technology. More specifically, the antibody of the present application has a $K_D$ ratio at pH 7.4/pH 6.0 of greater than 2, 3, 4, 5, 6, 7, 8, 9, 10, 20, 30, 40, 50, 60, 70, 80, 90, 100, or more, as measured by surface plasmon resonance (Biacore) or similar technology. Alternatively or additionally, the antibody of the present application has a Rmax (RU) value at pH 6.0 which is at least 2-fold, 3-fold, 4-fold, 5-fold, 6-fold, 7-fold, 8-fold, 9-fold, 10-fold, 20-fold, 30-fold, 40-fold, 50-fold higher than the Rmax at pH 7.4 as measured by surface plasmon resonance (Biacore) or similar technology. The binding affinity of the antibody can be measured at 25° C. or 37° C. Tumor microenvironment has been found to show a relatively more acidic pH than physiological condition or normal tissues (Zhang et al. Focus on molecular Imaging 2010; Tannock and Rotin et al. Cancer Res 1989). Therefore, the antibody of the present application having above-mentioned pH-dependent binding is advantageous as an anti-TIGIT therapeutic agent for targeting TIGIT-positive lymphocytes in the tumor microenvironment with selectivity and having lower toxicity associated with periphery activation of lymphocytes.

The term "human antibody" herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" means an antibody that comprises only mouse or rat immunoglobulin protein sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu", "Hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The antibody of the present application has potential therapeutic uses in treating cancer. The term "cancer" or "tumor" herein means or describes the physiological condition in mammals that is typically characterized by unregulated cell growth. Examples of cancer include but are not limited to, lung cancer (including small-cell lung cancer, or non-small cell lung cancer), adrenal cancer, liver cancer, stomach cancer, cervical cancer, melanoma, renal cancer, breast cancer, colorectal cancer, leukemia, bladder cancer, bone cancer, brain cancer, an endometrial cancer, head and neck cancer, lymphoma, ovarian cancer, skin cancer, thyroid tumor, or metastatic lesion of the cancer.

Further, the antibody of the present application has potential therapeutic uses in controlling viral infections and other human diseases that are mechanistically involved in immune tolerance or "exhaustion". In the context of the present application, the term "exhaustion" refers to a process which leads to a depleted ability of immune cells to respond to the infecting virus during a prolonged period of chronic viral infection.

Pharmaceutical Compositions and Kits

In some aspects, this disclosure provides compositions, e.g., pharmaceutically acceptable compositions, which include an anti-Tigit-3 antibody described herein, formulated together with at least one pharmaceutically acceptable excipient. As used herein, the term "pharmaceutically acceptable excipient" includes any and all solvents, dispersion media, isotonic and absorption delaying agents, and the like that are physiologically compatible. The excipient can be suitable for intravenous, intramuscular, subcutaneous, parenteral, rectal, spinal or epidermal administration (e.g. by injection or infusion).

The compositions herein may be in a variety of forms. These include, for example, liquid, semi-solid and solid dosage forms, such as liquid solutions (e.g., injectable and infusion solutions), dispersions or suspensions, liposomes, and suppositories. A suitable form depends on the intended mode of administration and therapeutic application. Typical suitable compositions are in the form of injectable or infusion solutions. One suitable mode of administration is parenteral (e.g., intravenous, subcutaneous, intraperitoneal, intramuscular). In some embodiments, the antibody is administered by intravenous infusion or injection. In certain embodiments, the antibody is administered by intramuscular or subcutaneous injection.

The term "therapeutically effective amount" as herein used, refers to the amount of an antibody that, when administered to a subject for treating a disease or a disorder, or at least one of the clinical symptoms of a disease or disorder, is sufficient to effect such treatment for the disease, disorder, or symptom. The "therapeutically effective amount" can vary with the antibody, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the active agents comprised in the combination for the effective treatment of a disease, a disorder or a condition.

The "subject" as used herein is a mammal, e.g., a rodent or a primate, preferably a higher primate, e.g., a human (e.g., a patient having, or at risk of having, a disorder described herein).

EXAMPLE

Example 1 Generation of Anti-Tigit Monoclonal Antibody

Anti-Tigit monoclonal antibodies (mAbs) were generated based on conventional hybridoma fusion technology [de StGroth and Sheidegger; 1980 *J Immunol Methods* 35:1; Mechetner, 2007 *Methods Mol Biol* 378:1] with minor modifications. The mAbs with high binding activity in enzyme-linked immunosorbent assay (ELISA) and fluorescence-activated cell sorting (FACS) assay were selected for further characterization.

Tigit Recombinant Protein for Immunization and Binding Assays

The cDNA coding for the full-length human Tigit (SEQ ID NO:1) was synthesized by and purchased from Sino Biological (Beijing, China) based on its GenBank sequence (Accession No: NM_173799). The coding region of extracellular domain (ECD) of the full-length human Tigit corresponding to the amino acid (AA) 1-141 of SEQ ID NO: 1 was PCR-amplified, and cloned into pcDNA3.1-based expression vector (Invitrogen, Carlsbad, Calif., USA) with C-terminus fused either to the Fc domain of mouse IgG2a or to the Fc domain of human IgG1 heavy chain, which resulted in two recombinant fusion protein expression plasmids, Tigit-mIgG2a and Tigit-huIgG1, respectively. The schematic presentation of Tigit fusion proteins were shown in FIG. 1. For the recombinant fusion protein production, Tigit-mIgG2a and Tigit-huIgG1 plasmids were transiently transfected into 293G cells (developed in-house) and cultured for 7 days in a $CO_2$ incubator equipped with rotating shaker. The supernatant containing the recombinant protein was collected and cleared by centrifugation. Tigit-mIgG2a and Tigit-huIgG were purified using a Protein A column (Cat.: 17127901, GE Life Sciences). Both Tigit-mIgG2a and Tigit-huIgG1 proteins were dialyzed against phosphate buffered saline (DPBS) and stored in −80° C. freezer in small aliquots.

Stable Expression Cell Lines

To establish stable cell lines that express full-length human Tigit (huTigit) or monkey Tigit (mkTigit, accession #: XM_005548101.2), Tigit genes (synthesized by Genescript, Nanjing, China) were cloned into a retroviral vector pFB-Neo (Cat.: 217561, Agilent, USA). Dual-tropic retroviral vectors were generated according to a previous protocol [Zhang T, et al. 2005, Blood]. Vectors containing huTigit and mkTigit were transduced into Jurkat and NK92MI cells (ATCC, Manassas, Va., USA), respectively, to generate the cell lines, Jurkat/huTigit and NK92MI/mkTigit. The high expression cell lines were selected by cultivation in medium with G418 and FACS binding assay.

Immunization, Hybridoma Fusion and Cloning

Eight to twelve week-old Balb/c mice (from HFK BIOSCIENCE CO., LTD, Beijing, China) were immunized intraperitoneally (i.p.) with 100 μL of antigen mixture containing 10 μg of Tigit-mIgG2a and a water-soluble adjuvant (Cat.: KX0210041, KangBiQuan, Beijing, China). The procedure was repeated three weeks later. Two weeks after the $2^{nd}$ immunization, mouse sera were evaluated for Tigit binding by ELISA and FACS. Ten days after serum screening, the mice with the highest anti-Tigit antibody serum titers were boosted via i.p. injection with 50 μg of Tigit-mIgG2a. Three days after boosting, the splenocytes were isolated and fused to the murine myeloma cell line, SP2/0 cells (ATCC), using the standard techniques [1977 *Somat Cell Genet*, 3:231].

Assessment of Tigit Binding Activity of Antibodies by ELISA and FACS

The supernatants of hybridoma clones were initially screened by ELISA as described in "Methods in Molecular Biology (2007) 378:33-52" with some modifications. Briefly, Tigit-huIgG1 protein was coated in 96-well plates. The HRP-linked anti-mouse IgG antibody (Cat.: 7076S, Cell Signaling Technology, USA) and substrate (Cat.: 00-4201-56, eBioscience, USA) were used to develop color absorbance signal at the wavelength of 450 nm, which was measured by using a plate reader (SpectraMax Paradigm, Molecular Devices, USA). The ELISA-positive clones were further verified by FACS using either NK92MI/huTigit or NK92mi/mkTigit cells described above. Tigit-expressing cells ($10^5$ cells/well) were incubated with ELISA-positive hybridoma supernatants, followed by binding with Alexa Fluro-647 labeled goat anti-mouse IgG antibody (Cat.: A0473, Beyotime Biotechnology, China). Cell fluorescence was quantified using a flow cytometer (Guava easyCyte 8HT, Merck-Millipore, USA).

The conditioned media from the hybridomas that showed positive signals in both ELISA and FACS screening were subjected to functional assays to identify antibodies with good functional activity in human immune cell-based assays (see following sections). The antibodies with desired functional activities were further sub-cloned and characterized.

Subcloning and Adaptation of Hybridomas to Serum-Fee or Low Serum Medium

After primary screening by ELISA, FACS and functional assays as described above, the positive hybridoma clones were sub-cloned by the limiting dilution. Three positive subclones based on ELISA and FACS screening from each plate were selected and characterized by functional assays. The top antibody subclones verified through functional assays were adapted for growth in the CDM4MAb medium (Cat.: SH30801.02, Hyclone, USA) with 3% FBS.

Expression and Purification of Monoclonal Antibodies

Hybridoma cells or 293G cells transiently transfected with an antibody expression plasmid (Cat. No. R79007, Invitrogen) was cultured either in CDM4MAb medium (Cat.: SH30801.02, Hyclone) or in Freestyle™ 293 Expression medium (Cat.: 12338018, Invitrogen), and incubated in a $CO_2$ incubator for 5 to 7 days at 37° C. The conditioned medium was collected through centrifugation and filtrated by passing a 0.22 μm membrane before purification. Murine or recombinant antibodies containing supernatants were applied and bound to a Protein A column (Cat.: 17127901, GE Life Sciences) following the manufacturer's guide. The procedure usually yielded antibodies at purity above 90%. The Protein A-affinity purified antibodies were either dialyzed against PBS or further purified using a HiLoad 16/60 Superdex200 column (Cat.: 17531801, GE Life Sciences) to remove aggregates. Protein concentrations were determined by measuring absorbance at 280 nm. The final antibody preparations were stored in aliquots in −80° C. freezer.

Example 2 Cloning and Sequence Analysis of Tigit Antibodies

Murine hybridoma clones were harvested to prepare total cellular RNAs using Ultrapure RNA kit (Cat.: 74104, QIAGEN, Germany) based on the manufacturer's protocol. The 1$^{st}$ strand cDNAs were synthesized using a cDNA synthesis kit from Invitrogen (Cat.: 18080-051) and PCR amplification of the nucleotide sequences coding for heavy chain variable region (Vh) and kappa chain variable region (VA) of murine mAbs was performed using a PCR kit (Cat.: CW0686, CWBio, Beijing, China). The oligo primers used for antibody cDNAs cloning of Vh and Vk were synthesized by Invitrogen (Beijing, China) based on the sequences reported previously (Brocks et al. 2001 Mol Med 7:461). PCR products were then subcloned into the pEASY-Blunt cloning vector (Cat.:C B101-02, TransGen, China) and sequenced by Genewiz (Beijing, China). The amino acid sequences of Vh and Vk regions were deduced from the DNA sequencing results.

Figure 2:
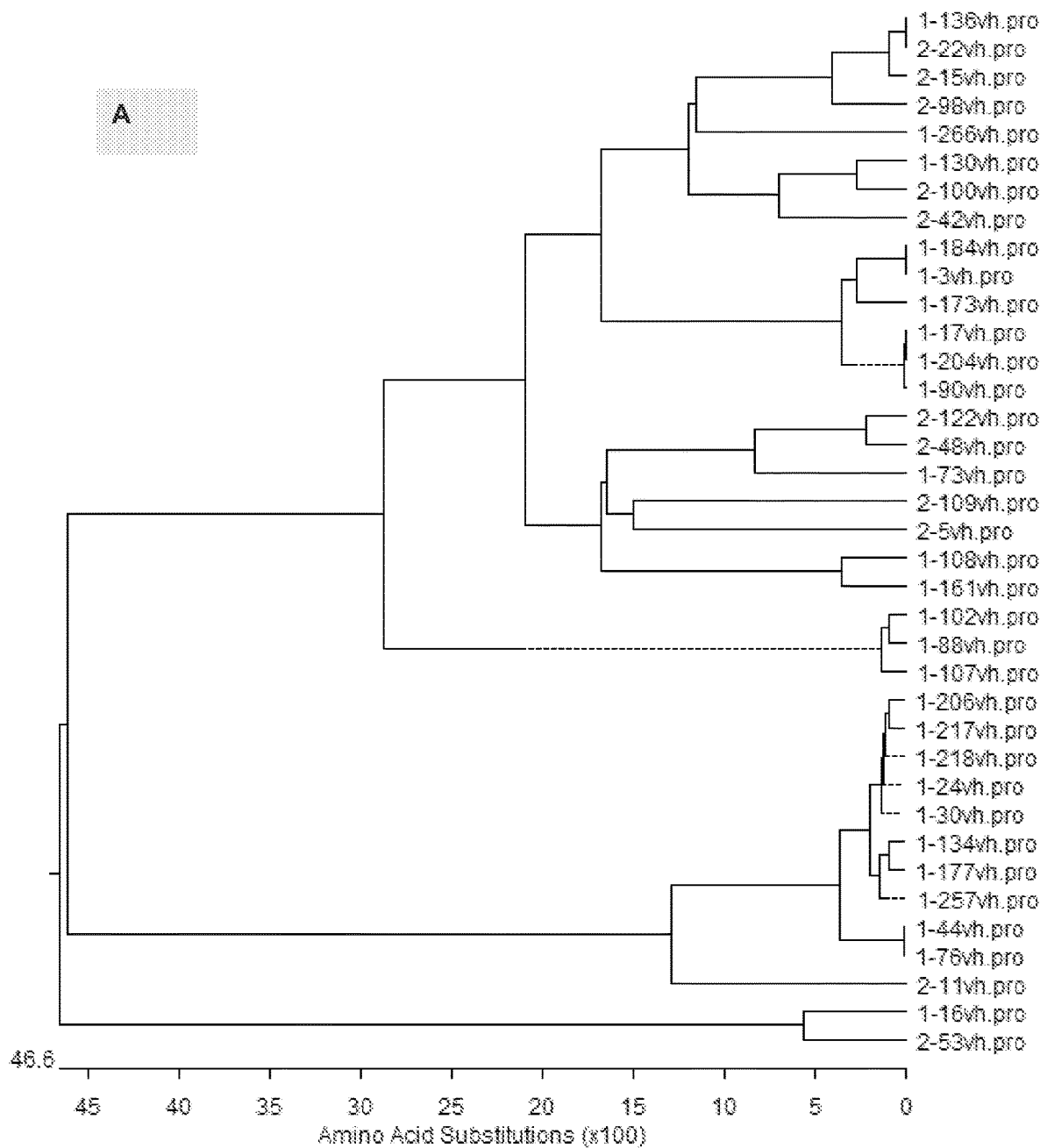
FIG. 2 Phylogenetic trees of anti-Tigit antibody Vh (A) and Vk (B) regions. The Vh and Vk sequences of candidate anti-Tigit antibodies were aligned using DNASTAR's Megalign software. Sequence homology was displayed in phylogenetic trees.
Figure 2:
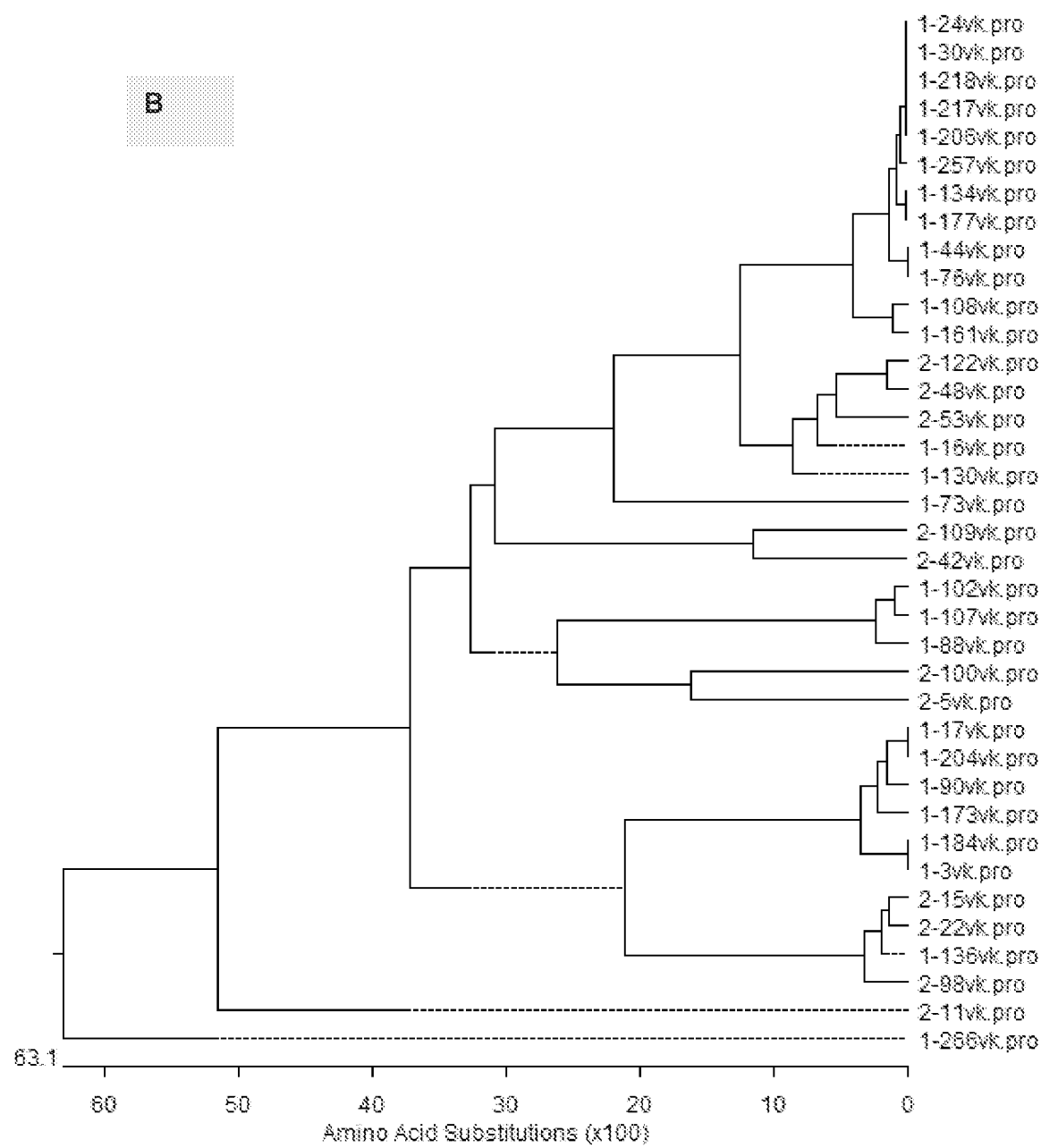

The murine mAbs were analyzed by comparing sequence homology and grouped based on sequence similarity (FIG. 2). Complementary determinant regions (CDRs) were defined based on the Kabat [Wu and Kabat 1970 1 Exp. Med. 132:211-250] and IMGT [Lefranc 1999 Nucleic Acids Research 27:209-212] system by sequence annotation and by internet-based sequence analysis in IGMT. The amino acid sequences of a representative top clone mu1217 (Vh and Vk) were listed in Table 1 (SEQ ID NOs:

9 and 11). The CDR sequences of mu1217 were listed in Table 2 (SEQ ID NOs: 3-8).

TABLE 1

Amino acid sequences of mu1217 Vh and Vk regions

| | |
|---|---|
| mu1217 Vh | SEQ ID NO 9 |
| mu1217 Vk | SEQ ID NO 11 |

TABLE 2

CDR sequences (amino acids) of mu1217 Vh and Vk regions

| mAbs | CDR1 | CDR2 | CDR3 |
|---|---|---|---|
| mu1217, Vh | SEQ ID NO 3 | SEQ ID NO 4 | SEQ ID NO 5 |
| mu1217, Vk | SEQ ID NO 6 | SEQ ID NO 7 | SEQ ID NO 8 |

Note:
CDR sequences are defined based on Kabat system

Figure 3:
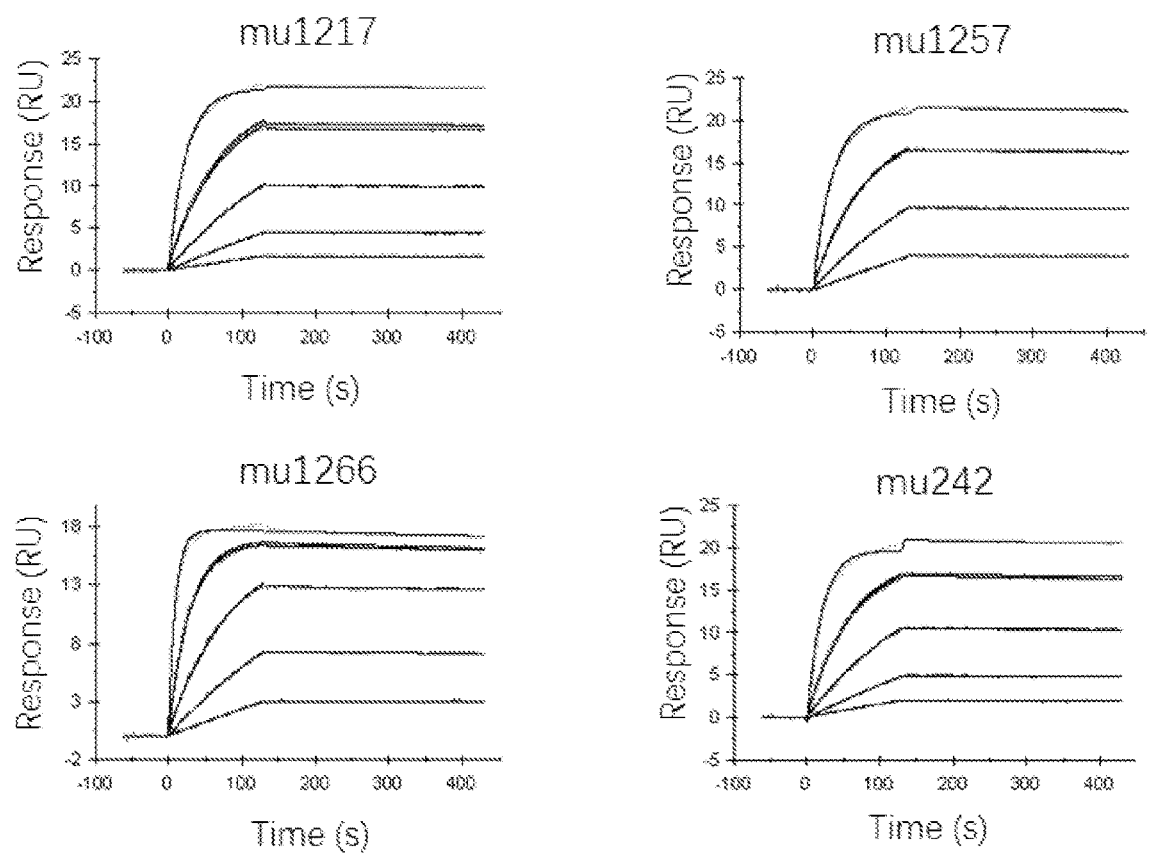
FIG. 3 Affinity determination of purified murine anti-Tigit antibodies by surface plasmon resonance (SPR).

Example 3 Affinity Determination of Purified Murine Anti-Tigit Antibodies by SPR The Tigit antibodies with high binding activities in ELISA and FACS, as well as with potent functional activities in the cell-based assays (described in Examples 1 and 2) were characterized for their binding kinetics by SPR assays using BIAcore™ T-200 (GE Life Sciences). Briefly, anti-human IgG antibody was immobilized on an activated CM5 biosensor chip (Cat. No.: BR100530, GE Life Sciences). Human Fc-tagged Tigit was flowed over the chip surface and captured by anti-human IgG antibody. Then a serial dilution (0.12 nM to 10 nM) of purified murine antibodies were flowed over the chip surface and changes in surface plasmon resonance signals were analyzed to calculate the association rates ($k_{on}$) and dissociation rates ($k_{off}$) by using the one-to-one Langmuir binding model (BIA Evaluation Software, GE Life Sciences). The equilibrium dissociation constant (K)) was calculated as the ratio $k_{off}/k_{on}$. The binding affinity profiles of top mAbs including mu1217, mu1257, mu1226 and mu242, were shown in FIG. 3 and Table 3.

TABLE 3

Binding affinities of hybridoma antibodies by SPR

| Antibodies | $k_{on}$ ($M^{-1}s^{-1}$) | $k_{off}$ ($s^{-1}$) | $K_D$ (nM) |
|---|---|---|---|
| mu1217 | 4.33E+06 | 3.96E−05 | 9.15E−12 |
| mu1257 | 3.99E+06 | 4.20E−05 | 1.05E−11 |
| mu1266 | 1.07E+07 | 8.49E−05 | 7.94E−12 |
| mu242 | 5.12E+06 | 7.13E−05 | 1.39E−11 |

Example 4 Humanization of the Murine Anti-Human Tigit mAb Mu1217 mAb Humanization and Engineering

For humanization of the mu1217, human germline IgG genes were searched for sequences that share high degrees of homology to the cDNA sequences of mu1217 variable regions by blasting the human immunoglobulin gene database in IMGT and NCBI websites. The human IGVH and IGVK genes that are present in human antibody repertoires with high frequencies (Glanville 2009 PNAS 106:20216-20221) and are highly homologous to mu1217 were selected as the templates for humanization.

Humanization was carried out by CDR-grafting (Methods in Molecular Biology, Vol 248: Antibody Engineering, Methods and Protocols, Humana Press) and the humanization antibodies (hu1217s) were engineered as the human IgG1mf format using an in-house developed expression vector. In the initial round of humanization, mutations from murine to human amino acid residues in framework regions were guided by the simulated 3D structure, and the murine framework residues of structural importance for maintaining the canonical structures of CDRs were retained in the 1⁴ version of humanization antibody 1217 (hu1217-1-1, with six CDRs having amino acid sequences of SEQ ID NOs: 3, 13, 5 (heavy chain CDRs) and SEQ ID NOs: 6, 7, 8 (light chain CDRs), a heavy chain variable region having an amino acid sequence of SEQ ID NO: 14 and encoded by a nucleotide sequence of SEQ ID NO: 15, and a light chain variable region having an amino acid sequence of SEQ ID No:16 and encoded by a nucleotide sequence of SEQ ID NO: 17). Specifically, CDRs of mu1217 Vκ (SEQ ID NO: 6-8) were grafted into the framework of human germline variable gene IGVκ3-15 with 1 murine framework residue ($V_{58}$) retained, resulting in the humanized Vκ sequence of Hu1217-1-1 (SEQ ID NO: 16 for amino acid sequence and SEQ ID NO: 17 for nucleotide sequence). N-terminal of H-CDR2 (SEQ ID NO: 4), H-CDR1 and H-CDR3 (SEQ ID NOs: 3 and 5) of mu1217 Vh were grafted into the framework of human germline variable gene IGVH3-7 with two murine framework ($T_{24}$ and I37 of SEQ ID NO: 10) residues retained. In the hu1217 humanization variants, only the N-terminal half of Kabat H-CDR2 was grafted, as only the N-terminal half was predicted to be important for antigen binding according to the simulated 3D structure. The amino acid sequence and nucleotide sequence of the resultant humanized Vh sequence of Hu1217-1-1 are shown in SEQ ID NO: 14 and SEQ ID NO: 15, respectively.

Hu1217-1-1 were constructed as human full-length antibody format using in-house developed expression vectors that contain constant regions of a human IgG1 variant termed as IgG1mf (SEQ ID NO: 18) and kappa chain, respectively, with easy adapting sub-cloning sites. Expression and preparation of hu1217-1-1 antibody was achieved by co-transfection of the above two constructs into 293G cells and by purification using a protein A column (Cat.: 17543802, GE Life Sciences). The purified antibodies were concentrated to 0.5-5 mg/mL in PBS and stored in aliquots in −80° C. freezer.

Based on hu1217-1-1 template, we made several single-mutations converting the retained murine residues in framework region of Vκ to corresponding human germline residues, which include V58I in Vκ and in T24A and 137V Vh. The resulted hu1217-2A-1 (T24A), hu1217-2B-1 (I37V), and hu1217-1-2a (V58I) all had similar binding and functional activities to hu1217-1-1. All humanization mutations were made using primers containing mutations at specific positions and a site directed mutagenesis kit (Cat. No. FM111-02, TransGen, Beijing, China). The desired mutations were verified by sequencing analysis. These hu1217-derived variant antibodies were tested in binding and functional assays as described previously.

Hu1217 antibodies were further engineered by introducing mutations in CDRs and framework regions to improve molecular and biophysical properties for therapeutic use in human. The considerations include amino acid compositions, heat stability (Tm), surface hydrophobicity and isoelectronic points (pIs) while maintaining functional activities.

Taken together, a well-engineered version of humanized monoclonal antibody, hu1217-2-2 (SEQ ID NOs:3, 5-8, 13, and 19-21), was derived from the mutation process described as above, and characterized in detail. The results showed both hu1217-2-2 and hu1217-1-1 were very similar in binding affinity and functional activities such as inhibiting the Tigit-mediated downstream signaling.

For affinity determination, antibodies were captured by anti-human Fc surface, and used in the affinity-assay based on surface plasmon resonance (SPR) technology. The results of SPR-determined binding profiles of anti-Tigit antibodies were summarized in Table 4. Hu217-2-2 and hu1217-1-1 showed very similar binding profiles with average dissociation constant at 0.415 nM and 0.266 nM, respectively, which are close to that of ch1217.

TABLE 4

Binding affinities of hu1217 antibodies by SPR

| Antibodies | Test 1 | | | Test 2 | | | Mean |
|---|---|---|---|---|---|---|---|
| | $k_{on}$ (M⁻¹s⁻¹) | $k_{off}$ (s⁻¹) | $K_D$ (nM) | $k_{on}$ (M⁻¹s⁻¹) | $k_{off}$ (s⁻¹) | $K_D$ (nM) | $K_D$ (nM) |
| ch1217* | 1.56 × 10⁶ | 4.43 × 10⁻⁴ | 0.283 | — | — | — | NA** |
| hu1217-1-1 | 1.45 × 10⁶ | 4.48 × 10⁻⁴ | 0.309 | 1.33 × 10⁶ | 6.94 × 10⁻⁴ | 0.520 | 0.415 |
| hu1217-2-2 | 1.80 × 10⁵ | 2.29 × 10⁻⁴ | 0.127 | 1.50 × 10⁶ | 6.08 × 10⁻⁴ | 0.404 | 0.766 |

*ch1217 is comprised of mu1217 variable domains fused to human IgG1mf/kappa constant regions
**NA: not available.

TABLE 5

CDRs of hu1217 antibodies

| Antibodies | CDR1 | CDR2 | CDR3 |
|---|---|---|---|
| hu1217-1-1, Vh | SEQ ID NO 3 | SEQ ID NO 13 | SEQ ID NO 5 |
| hu1217-2-2, Vh | SEQ ID NO 3 | SEQ ID NO 13 | SEQ ID NO 5 |
| hu1217-1-1, Vκ | SEQ ID NO 6 | SEQ ID NO 7 | SEQ ID NO 8 |
| hu1217-2-2, Vκ | SEQ ID NO 6 | SEQ ID NO 7 | SEQ ID NO 8 |

All the humanization antibodies shown above were also confirmed for functional activities on primary human immune cells isolated from healthy donors (described in Example 7).

Example 5 Binding Activities of Different Versions of 1217 to Native Tigit

Figure 4:
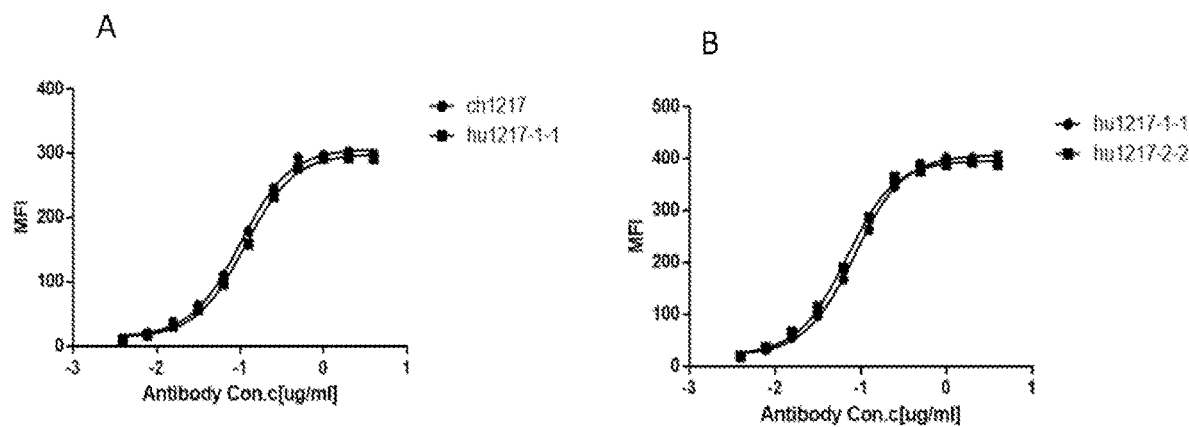
FIG. 4 Determination of Tigit binding by flow cytometry.

To evaluate the binding activity of anti-Tigit antibodies to native Tigit on living cells, NK92mi cells were engineered to over-express human Tigit. Living NK92mi/Tigit cells were seeded in 96-well plate, and were incubated with a series of dilutions of anti-Tigit antibodies. Goat anti-Human IgG was used as secondary antibody to detect antibody binding to the cell surface. $EC_{50}$ values for dose-dependent binding to human native Tigit were determined by fitting the dose-response data to the four-parameter logistic model with GraphPad Prism. As show in FIG. 4 and Table 6. Both humanized 1217 antibodies, hu217-1-1 and hu217-2-2, showed good binding affinity to native Tigit on living cells.

TABLE 6

EC$_{50}$ of dose-dependent binding of humanized 1217 variants to native Tigit

| Antibodies | EC$_{50}$(ug/mL) | |
|---|---|---|
| | Test 1 | Test 2 |
| Ch1217 | 0.100 | — |
| hu1217-1-1 | 0.114 | 0.084 |
| hu1217-2-2 | | 0.068 |

Example 6 Anti-Tigit Antibodies Block the Interactions of Tigit with its Ligands PVR and PVR-L2

Tigit binds to PVR with a high affinity (Kd: ~1 nM), which can compete against CD266-PVR interaction [Yu et al., 2009].

Figure 5:
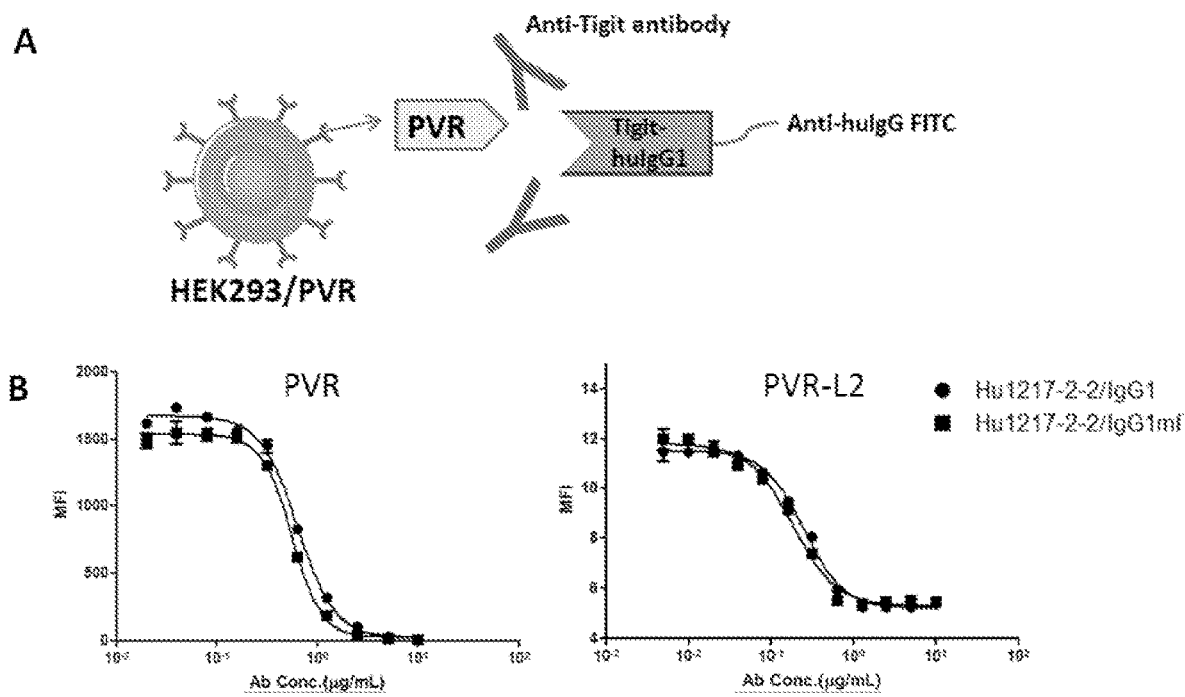
FIG. 5 (A) A schematic diagram showing the inhibition of Tigit-ligand interactions by anti-Tigit mAbs. (B) The binding of soluble Tigit (Tigit-huIgG1 fusion protein) to Tigit ligand-expressing HEK293 cells (HEK293/PVR or HEK293/PVR-L2) was determined by flow cytometry. The blockade of Tigit-ligand interaction was quantitatively measured by adding serially diluted anti-Tigit antibodies. Results were shown in mean±SD of duplicates.

To determine whether anti-Tigit antibodies could block Tigit-PVR and Tigit-PVR-L2 interactions, HEK293 cells were engineered to express high levels of PVR or PVR-L2. The resultant cell lines were named HEK293/PVR and HEK293/PVR-L2, respectively. The binding of soluble Tigit (Tigit-mIgG2a fusion protein) to PVR or PVR-L2 was determined by flow cytometry (FIG. 5A). The blockade of Tigit-ligand interaction was quantitatively measured by adding serially diluted anti-Tigit antibodies. As shown in FIG. 5B, hu1217-2-2/IgG1 (a humanized version comprising a wild-type IgG1 Fc region and having the same VH and VL sequences as hu1217-2-2/IgG1mf) and hu1217-2-2/IgG1mf could block Tigit binding to PVR in a dose-dependent manner with IC$_{50}$ at 0.64 and 0.55 µg/mL, respectively. Similarly, the IC$_{50}$ of hu1217-2-2/IgG1 and hu1217-2-2/IgG1mf in blocking Tigit-PVR-L2 interaction is 0.25 and 0.18 µg/mL, respectively.

Example 7 Activation of CMV-Specific Human T Cells by Anti-Tigit Antibodies

Figure 6:
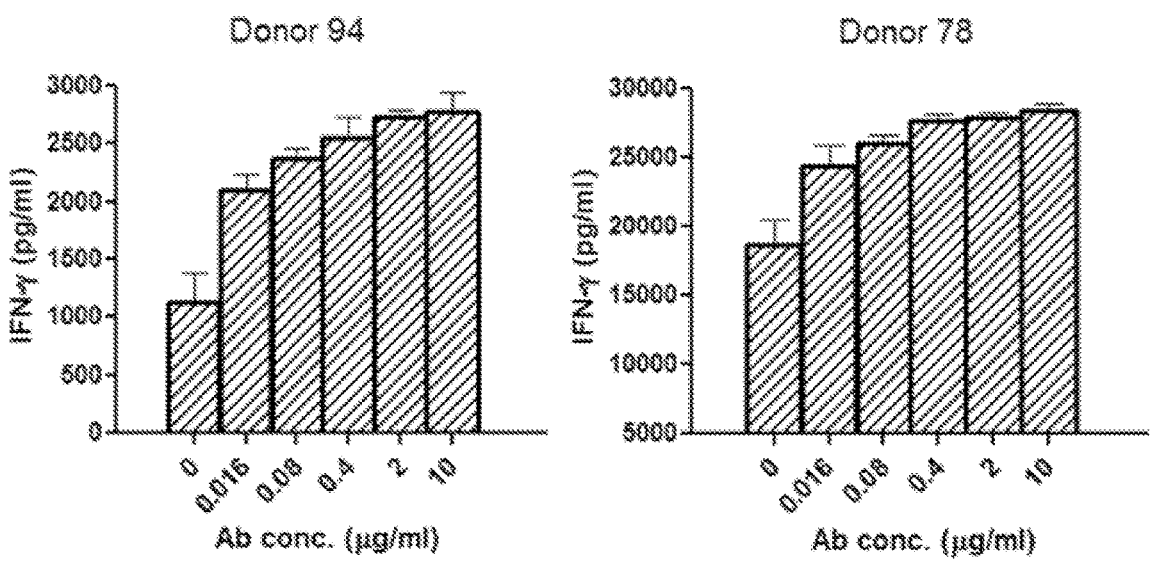
FIG. 6 Activation of CMV-specific human T cells by anti-Tigit mAbs. Human CMV peptide (NLVPMVATV, 495-503)-sensitized HLA-A2.1$^+$ PBMCs ($4\times10^4$) were stimulated with the CMV peptide-pulsed target cells HCT116 cells ($10^4$) overnight in the presence of anti-Tigit antibodies. IFN-γ in the culture supernatant was determined by ELISA. All conditions were performed in triplicates. Results were shown as mean SD.

The functional activity of the Tigit antibodies were further assessed using naturally derived T-cells that recognized human CMV PP65 peptide (NLVPMVATV, 495-503, HLA-A2.1-restricted) [Boeckh M, Boeckh M and Geballe A P 2011 *J Clin Invest.* 121:1673-80]. Briefly, PBMCs from HLA-A2.1+ healthy donors were simulated with PP65 peptide (>98% purity, synthesized by GL Biochem, Shanghai) in the complete RPMI with 10% FBS for a week. The pp65-primed PBMCs were used as effector cells. Prior to assay, target cells, HCT116 cells (HLA-A2.1+, 10$^4$), were pulsed with pp65 peptide (5 µg/mL) for 30 mins and co-cultured with equal numbers of pp65-sensitized PBMCs in 96-well plates overnight in the presence or absence of anti-Tigit antibodies or a blank control (medium only). As shown in FIG. 6, hu217-2-2/IgG1 promoted pp65-specific T cells to secrete IFN-γ in the cell culture supernatant in a dose-dependent manner for both donors.

Example 8 Anti-Tigit Antibodies Enhanced NK Cell-Mediated Cytotoxicity

Tigit is known to be constitutively expressed on natural killer (NK) cells at relatively higher levels and the interaction between Tigit and its ligands inhibits NK cell-mediated cytotoxicity [Wang F et al. 2015 *Eur. J. Immunology* 45:2886-97, Stanietsky N et al., 2009 *Proc Natl Acad Sci USA* 106:17858-63].

To confirm whether humanized anti-Tigit antibodies could promote NK-mediated cytotoxicity, an NK cell line NK92M1 was engineered to co-express both Tigit and DNAM-1 receptors (NK92M1/Tigit-DNAM-1) as an effector cell by retroviral transduction, according to the protocols described previously [Zhang et al, 2006 *Cancer Res.* 66: 5927-5933]. A PVR-expressing lung cancer cell line SK-MES-1/PVR was established similarly as a target.

Figure 7:
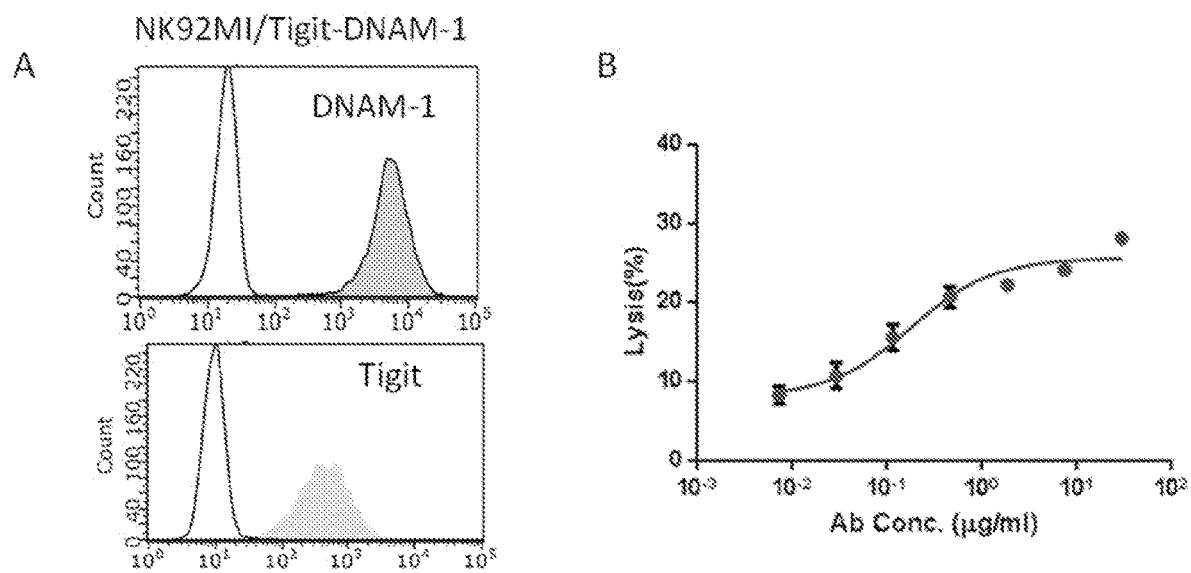
FIG. 7 Anti-Tigit mAbs promote NK cell-mediated cytotoxicity. (A) Tigit and DNAM-1 expression on engineered NK92MI/Tigit-DNAM-1 stable cell line. (B) Killing of NK92MI/Tigit-DNAM-1 cells against SK-MES-1/PVR cells in the presence of hu1217-2-2/IgG1mf (0.007-30 μg/ml) was determined by an LDH (lactate dehydrogenase) release assay as described in Example 8. Results were shown in mean±SD of triplicates.

Cytotoxicity of NK92MI/Tigit-DNAM-1 cells against SK-MES-1/PVR cells was determined by an LDH release assay using the CytoTox 96 Non-Radioactive Cytotoxicity Assay kit (Promega, Madison, Wis.). In brief, NK92MI/Tigit-DNAM-1 cells (8×10$^5$) were co-cultured with SK-MES-1/PVR cells (2×10$^4$) in the presence of anti-Tigit Abs (0.007-30 µg/mL) for 5 hr in 96-well V-bottom plates. LDH-release assay Specific lysis was determined using the following equation: percentage of specific lysis=[(experimental-effector spontaneous-target spontaneous)/(target maximum−target spontaneous)]×100. The results showed that anti-Tigit antibodies hu1217-2-2/IgG1mf enhances NK cell killing in a dose-dependent manner (EC$_{50}$: 0.185 g/mL) (FIG. 7).

Figure 8:
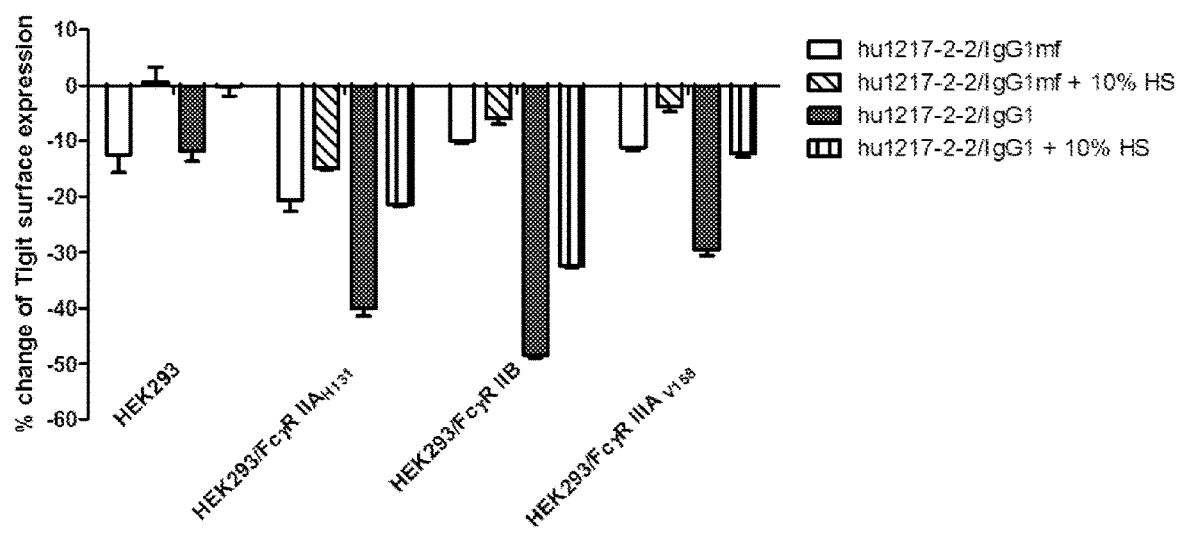
FIG. 8 Anti-Tigit mAb hu1217-2-2/IgG1 wt reduces the surface expression of Tigit receptor via FcγR-mediated trogocytosis. Jurkat/Tigit cells were incubated with Fc γ R-expressing HEK293 cells in the presence of biotin-labeled anti-Tigit mAbs in complete media overnight. In some cases, 10% human AB serum was added to determine the effects of bulk human IgG on trogocytosis. Surface expression of Tigit receptor was determined by staining with SA-APC (Biolegend). MFI was determined by flow cytometry. All data points were in duplicates. Results were shown in mean±SD.

Example 9 Anti-Tigit Antibodies can Reduce the Surface Expression of Tigit Receptor Via FcγR-Mediated Trogocytosis Trogocytosis is a phenomenon, in which cell surface molecules are transferred from donor cells to acceptor cells [Joly E, et al. 2003 *Nat. Immunol*; Machlenkin A. et al. 2008 *Cancer Res.*; Beum P V et al. 2008 *J. Immunol*; Rossi E A, et al. 2013 Blood]. Antibody-induced trogocytosis via Fe γ receptors (FcγRs) leads to down-modulation of receptors on the cell surface [Carlsten M, et al. 2016 *Clin Cancer Res*; Beum P V et al. 2011 *J. Immunology*]. Therefore, down-regulation of target receptor by trogocytosis may cause dampened signaling. In view of these observations, it would be possible that hu1217-2-2/IgG1 might induce trogocytosis of Tigit receptor in the presence of FcγR+ cells, resulting in lower surface expression. To address this possibility, Jurkat/Tigit cells were incubated with HEK cells expressing various FcγRs (including FcγRIIA$_{H131}$, FcγRIIB, FcγRIIIA$_{V158}$) with biotin-labeled hu1217-2-2/IgG1 wt (a humanized antibody comprising the same VL and VH sequences as hu1217-2-2/IgG1mf and a wild-type IgG1 Fc region) or hu1217-2-2/IgG1mf overnight. Surface expression of Tigit receptor was determined by with SA-APC (Biolegend). As shown in FIG. 8, hu1217-2-2/IgG1 but not hu1217-2-2/IgG1mf caused a significant reduction of Tigit surface expression compared to the negative control human IgG-treated cells, indicating that the reduction of surface Tigit on Jurkat/Tigit cells are FcγR-binding dependent. In addition, presence of 10% human serum (containing high-level of endogenous IgG) could partially reduce FcγRIIA$_{H131}$- or FcγRIIIA$_{V158}$-, but not FcγRIIB-mediated trogocytosis of Tigit receptor, suggesting that FcγRIIB could play a critical role reducing Tigit surface expression by anti-Tigit mAbs (e.g., hu1217-2-2/IgG1 wt) in vivo. These observations are also consistent with previous findings [Ganesan L P, et al. 2012 *J Immunol* 189:498-8; Taylor R P et al. 2015 *Blood* 125:762-6].

Example 10 ADCC and CDC Effector Functions of Anti-Tigit Antibodies

The abilities of anti-Tigit antibodies to induce ADCC and CDC in human primary PBMCs were determined using in vitro assay as described below.

ADCC Using Human PBMCs as Target Cells

Figure 9:
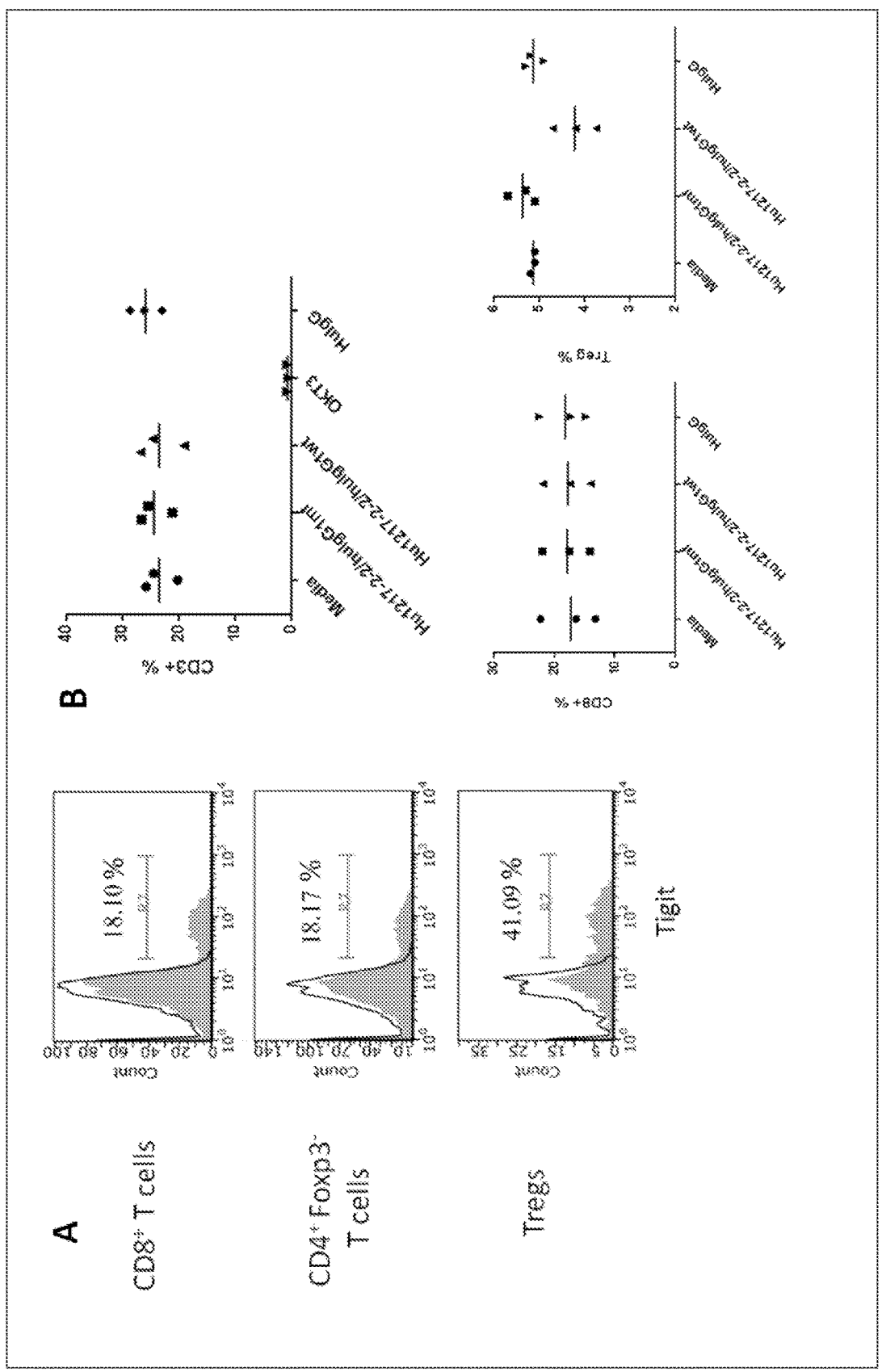
FIG. 9 ADCC effects of anti-Tigit mAbs on human peripheral blood mononuclear cells (PBMCs). (A) Tigit expression on PHA-stimulated PBMCs from healthy donors was determined by flow cytometry. CD4$^+$ (CD4$^+$Foxp3$^-$), CD8$^+$ T effectors and regulatory T cells (Tregs, CD4$^+$ Foxp3$^+$) all expressed significant levels of Tigit (18~41%). Data shown are representative results from 3 healthy donors. (B) ADCC assay was performed using a CD16$^+$ human NK cell line NK92MI/CD16V as effector cells and PHA-stimulated PBMCs as target cells in the presence of Tigit mAbs (30 μg/mL) or control antibodies (OKT3 at 5 μg/ml as a positive control, and huIgG at 30 μg/ml as a negative control) for 42 hrs. Percentages of CD3$^+$, CD8$^+$ T cells and Tregs were determined by flow cytometry.

A flow cytometry-based ADCC assay was set up to determine whether Tigit antibodies could induce ADCC in Tigit+ T cells. The assay effector cell line, NK92MI/CD16V cells, was generated from NK92MI cells (ATCC) by co-transducing expression plasmids containing CD16r se (V158 allele) and FcRγ cDNAs. Human PBMCs from healthy donors were stimulated with PHA (1 μg/ml) to up-regulate Tigit expression. As shown in FIG. 9, T cells, including CD4+ effector (CD3+CD4+Foxp3−), CD8+ and regulator T cells (CD4+Foxp3+) all expressed significant amounts of Tigit. These activated PBMCs (from 3 healthy donors) were used as target cells. A fluorescent dye CFSE-labeled NK92MI/CD16V cells (5×10^4) were co-cultured with equal number of target cells, for 40 hours in the presence of Tigit antibodies (hu1217-2-2/IgG1mf or hu1217-2-2/IgG1 wt, 30 μg/mL) or control antibodies (the positive control anti-CD3 antibody OKT3 (5 μg/ml, Biolegend) or a negative control human IgG, 30 μg/mL). Compared with human IgG and hu217-2-2/IgG1mf, hu1217-2-2/IgG1 wt could lead to moderate reduction of Tregs via ADCC. However, no significant ADCC effects were observed in total T cells and CD8+ T cells (FIG. 9).

CDC Using Human PBMCs as Target Cells

Figure 10:
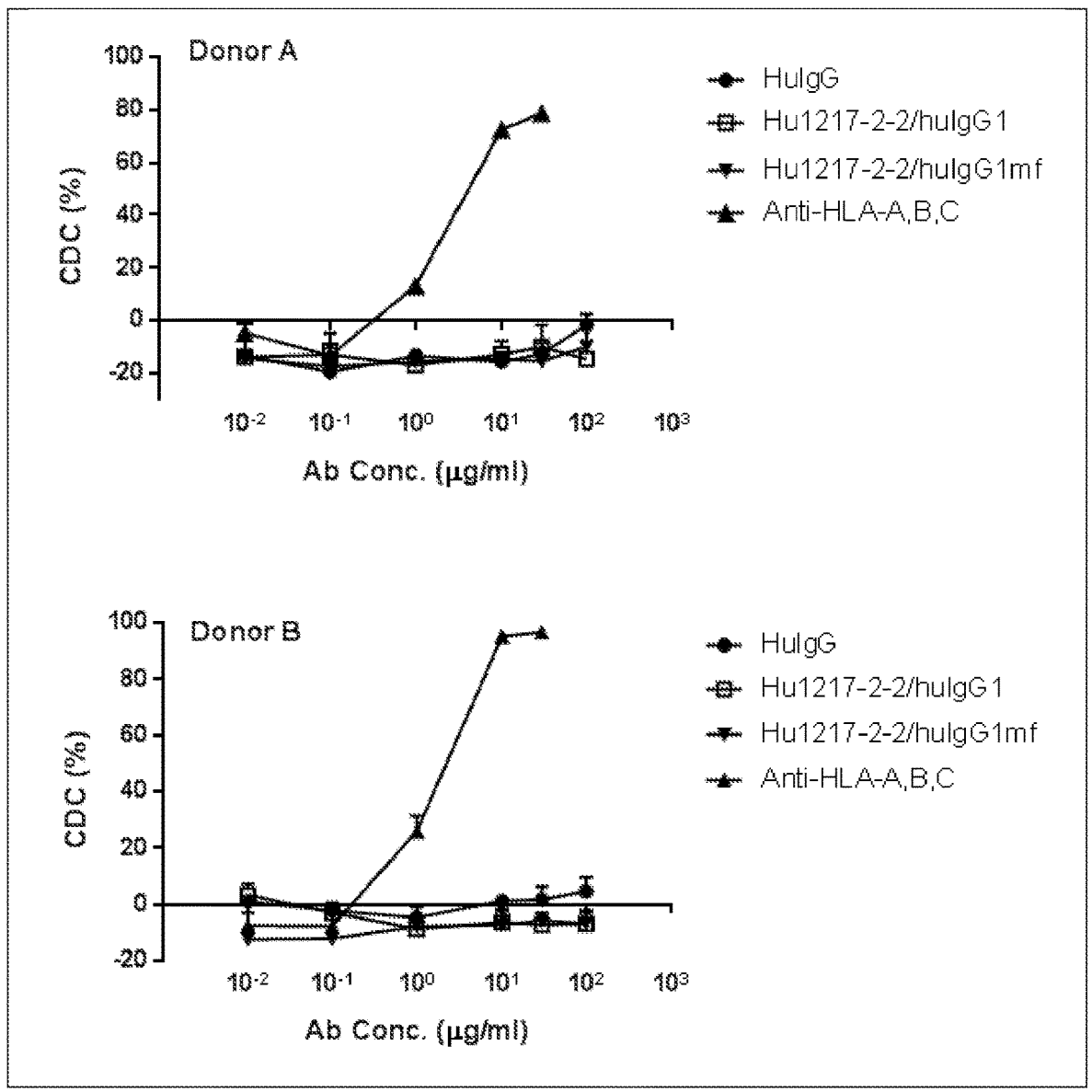
FIG. 10. CDC effects of anti-Tigit mAbs on human PBMCs. CDC assay was performed using PHA-stimulated PBMCs as target cells and autologous sera as the source of complements. After 3 days of co-culture of pre-activated PBMCs with anti-Tigit mAbs (0.01-100 μg/ml) in the final concentration of 1$^5$% autologous sera, percentage of CDC (y-axis) was measured by cell-titer glow assay, and calculated as described in Example 11. Data from donors A and B are shown. HuIgG were used as a negative control, whereas anti-MHC-A, B, C was used as a positive control.

Whether hu1217-2-2/IgG1mf and hu1217-2-2/IgG1 wt would trigger CDC was determined by using pre-activated human PBMCs and fresh autologous sera from healthy donors. Cell lysis by CDC was determined by a Celltiter glo assay kit (Promega, Beijing, China). In brief, PBMCs were pre-activated with PHA (10 μg/mL) for 3 days, and then were incubated in RPMI640 plus autologous serum (15%) and anti-Tigit or control antibodies (0.01-100 μg/mL) for overnight at 37° C. The cell death due to CDC was assayed by the decrease of ATP released from viable cells after cell lysis at the end of reaction. Anti-MHC-I A, B, C was used as a positive control. The fluorescence readout was conducted using a 96-well fluorometer (PHERA Star FS, BMG LABTECH), and the CDC activities were calculated from the relative fluorescence unit (RFU) readout as follows: % CDC activity=[(RFU test−RFU background)/(RFU at total cell lysis−RFU background)]×100. The experimental results demonstrated that both hu1217-2-2/IgG1mf and hu1217-2-2/IgG1 wt had no detactable CDC with PBMCs isolated from two different donors. In contrast, the positive control antibody, anti-MHC-1, induces significant CDC activity (FIG. 10).

Example 11 pH Dependent Binding Affinity of Hu1217-2-2/IgG1

To investigate whether pH would influence the binding property of hu1217-2-2/IgG1, target binding SPR tests were performed in running buffers at pH 7.4 and at pH 6.0 for comparison. The antibody hu1217-2-2/IgG1 was immobilized to a CM5 chip (GE). Serial dilutions of TIGIT-his were flown over the immobilized hu1217-2-2/IgG1 in running buffer HBS at pH 7.4 or pH 6.0.

As shown by the results listed in Table 7 below, hu1217-2-2/IgG1 showed higher binding affinity (KD) and stronger binding signal (Rmax) against human TIGIT at pH 6.0 (an acidic pH which is similar to the pH of tumor microenvironment) as compared to the data obtained at pH 7.4 (physiologic pH). These results indicate a potential advantage of the antibody as a therapeutic agent targeting TIGIT-positive lymphocytes in the tumor environment, since hu1217-2-2/IgG1 might more selectively target the TIGIT-positive lymphocytes in the tumor microenvironment while have lower potential toxicity associated with activation of periphery lymphocytes.

TABLE 7

Binding affinities of hu1217-2-2/IgG1 at pH7.4 and pH6.0 by SPR

| pH | $k_{on}$ (M$^{-1}$s$^{-1}$) | $k_{off}$ (s$^{-1}$) | $K_D$ (nM) | Rmax(RU) |
|---|---|---|---|---|
| 7.4 | 4.34E+05 | 9.53E−05 | 2.19E−10 | 21 |
| 6.0 | 2.54E+06 | 7.60E−05 | 2.99E−11 | 37 |

The invention claimed is:

1. An antibody or an antigen-binding fragment thereof, which is capable of binding to human Tigit, comprising:
   (a) a heavy chain variable region (VH) comprising heavy chain complementarity determining region (CDR)1, CDR2, and CDR3 comprising amino acid sequences of SEQ ID NOs: 3, 13, and 5, respectively; and
   (b) a light chain variable region (VL) comprising light chain CDR1, CDR2, and CDR3 comprising amino acid sequences of SEQ ID NOs: 6, 7 and 8, respectively.

2. The antibody or the antigen-binding fragment of claim 1, wherein the antibody is a humanized antibody molecule.

3. The antibody or the antigen-binding fragment of claim 1, comprising a heavy chain variable domain having at least 95%, 96%, 97%, 98%, or 99% sequence identity with the amino acid sequence of SEQ ID NO 14, and a light chain variable domain having at least 95%, 96%, 97%, 98%, or 99% sequence identity with the amino acid sequence of SEQ ID NO 16.

4. The antibody or the antigen-binding fragment of claim 1, comprising a heavy chain variable domain having at least 95%, 96%, 97%, 98%, or 99% sequence identity with the amino acid sequence of SEQ ID NO 19, and a light chain variable domain having at least 95%, 96%, 97%, 98%, or 99% sequence identity with the amino acid sequence of SEQ ID NO 21.

5. The antibody or the antigen-binding fragment of claim 1, comprising:
   (a) a heavy chain variable domain comprising the amino acid sequence of SEQ ID NO 14, and a light chain variable domain comprising the amino acid sequence of SEQ ID NO 16; or
   (b) a heavy chain variable domain comprising the amino acid sequence of SEQ ID NO 19, and a light chain variable domain comprising the amino acid sequence of SEQ ID NO 21.

6. The antibody or the antigen-binding fragment of claim 1, wherein the antibody comprises one or more of:
   (a) a heavy chain variable domain with a T to A mutation at position 24 of SEQ ID NO 14;
   (b) a heavy chain variable domain with a I to V mutation at position 37 of SEQ ID NO 14;
   (c) a light chain variable domain with a V to I mutation at position 58 of SEQ ID NO 16.

7. The antibody or the antigen-binding fragment of claim 1, wherein the antigen-binding fragment is a Fab, F(ab')2, Fv, or a single chain Fv(ScFv).

8. The antibody or the antigen-binding fragment of claim 1, comprising a heavy chain constant region of the subclass of IgG1, IgG2, IgG3, or IgG4 or a variant thereof, and a light chain constant region of the type of kappa or lambda or a variant thereof.

9. A pharmaceutical composition, comprising the antibody or the antigen-binding fragment of claim 1, and a pharmaceutically acceptable excipient.

10. The composition of claim 9, further comprising second therapeutic agent.

11. A method of stimulating an immune response in a subject in need thereof, comprising administrating to the subject the antibody or antigen-binding fragment of claim 1 in an amount effective to stimulate the immune response.

* * * * *

SEQUENCE LISTING

<160> NUMBER OF SEQ ID NOS: 24

<210> SEQ ID NO 1
<211> LENGTH: 244
<212> TYPE: PRT
<213> ORGANISM: Homo sapiens

<400> SEQUENCE: 1

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr

```
                100              105              110
Tyr Pro Asp Gly Thr Tyr Thr Gly Arg Ile Phe Leu Glu Val Leu Glu
            115              120              125

Ser Ser Val Ala Glu His Gly Ala Arg Phe Gln Ile Pro Leu Leu Gly
            130              135              140

Ala Met Ala Ala Thr Leu Val Val Ile Cys Thr Ala Val Ile Val Val
145              150              155              160

Val Ala Leu Thr Arg Lys Lys Lys Ala Leu Arg Ile His Ser Val Glu
            165              170              175

Gly Asp Leu Arg Arg Lys Ser Ala Gly Gln Glu Glu Trp Ser Pro Ser
            180              185              190

Ala Pro Ser Pro Pro Gly Ser Cys Val Gln Ala Glu Ala Ala Pro Ala
            195              200              205

Gly Leu Cys Gly Glu Gln Arg Gly Glu Asp Cys Ala Glu Leu His Asp
            210              215              220

Tyr Phe Asn Val Leu Ser Tyr Arg Ser Leu Gly Asn Cys Ser Phe Phe
225              230              235              240

Thr Glu Thr Gly

<210> SEQ ID NO 2
<211> LENGTH: 120
<212> TYPE: PRT
<213> ORGANISM: Homo sapiens

<400> SEQUENCE: 2

Met Met Thr Gly Thr Ile Glu Thr Thr Gly Asn Ile Ser Ala Glu Lys
1               5               10              15

Gly Gly Ser Ile Ile Leu Gln Cys His Leu Ser Ser Thr Thr Ala Gln
            20              25              30

Val Thr Gln Val Asn Trp Glu Gln Gln Asp Gln Leu Leu Ala Ile Cys
            35              40              45

Asn Ala Asp Leu Gly Trp His Ile Ser Pro Ser Phe Lys Asp Arg Val
        50              55              60

Ala Pro Gly Pro Gly Leu Gly Leu Thr Leu Gln Ser Leu Thr Val Asn
65              70              75              80

Asp Thr Gly Glu Tyr Phe Cys Ile Tyr His Thr Tyr Pro Asp Gly Thr
            85              90              95

Tyr Thr Gly Arg Ile Phe Leu Glu Val Leu Glu Ser Ser Val Ala Glu
            100             105             110

His Gly Ala Arg Phe Gln Ile Pro
            115             120

<210> SEQ ID NO 3
<211> LENGTH: 5
<212> TYPE: PRT
<213> ORGANISM: Mus musculus

<400> SEQUENCE: 3

Asp Tyr Tyr Met Tyr
1               5

<210> SEQ ID NO 4
<211> LENGTH: 17
<212> TYPE: PRT
<213> ORGANISM: Mus musculus

<400> SEQUENCE: 4
```

```
Tyr Ile Thr Lys Gly Gly Gly Ser Thr Tyr Tyr Pro Asp Thr Val Lys
 1               5                  10                  15

Gly

<210> SEQ ID NO 5
<211> LENGTH: 10
<212> TYPE: PRT
<213> ORGANISM: Mus musculus

<400> SEQUENCE: 5

Gln Thr Asn Tyr Asp Phe Thr Met Asp Tyr
 1               5                  10

<210> SEQ ID NO 6
<211> LENGTH: 11
<212> TYPE: PRT
<213> ORGANISM: Mus musculus

<400> SEQUENCE: 6

Lys Ala Ser Gln Asp Val Gly Thr Ser Val Ala
 1               5                  10

<210> SEQ ID NO 7
<211> LENGTH: 7
<212> TYPE: PRT
<213> ORGANISM: Mus musculus

<400> SEQUENCE: 7

Trp Ala Ser Ala Arg His Thr
 1               5

<210> SEQ ID NO 8
<211> LENGTH: 9
<212> TYPE: PRT
<213> ORGANISM: Mus musculus

<400> SEQUENCE: 8

Gln Gln Tyr Ser Ser Tyr Pro Leu Thr
 1               5

<210> SEQ ID NO 9
<211> LENGTH: 119
<212> TYPE: PRT
<213> ORGANISM: Mus musculus

<400> SEQUENCE: 9

Glu Val Lys Leu Val Glu Ser Gly Gly Leu Val Gln Pro Gly Gly
 1               5                  10                  15

Ser Leu Lys Leu Ser Cys Ala Thr Ser Gly Phe Thr Phe Ser Asp Tyr
                20                  25                  30

Tyr Met Tyr Trp Ile Arg Gln Thr Pro Glu Lys Arg Leu Glu Trp Val
            35                  40                  45

Ala Tyr Ile Thr Lys Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
 65                  70                  75                  80

Leu Gln Val Ser Arg Leu Lys Ser Glu Asp Thr Ala Ile Tyr Tyr Cys
                85                  90                  95

Ala Arg Gln Thr Asn Tyr Asp Phe Thr Met Asp Tyr Trp Gly Gln Gly
            100                 105                 110

Thr Ser Val Thr Val Ser Ser
```

<210> SEQ ID NO 10
<211> LENGTH: 357
<212> TYPE: DNA
<213> ORGANISM: Mus musculus

<400> SEQUENCE: 10

```
gaagtgaagc tggtggagtc tgggggaggc ttagtgcagc ctggagggtc cctgaaactc      60
tcctgtgcaa cctctggatt cactttcagt gactattaca tgtattggat tcggcagact     120
ccagagaaga ggctggagtg ggtcgcatac attactaagg gtggtggtag cacctattat     180
ccagacactg taaagggccg attcaccatc tccagagaca atgccaagaa caccctgtac     240
ctgcaagtga gccgtctgaa gtctgaggac acagccatat attactgtgc aagacagact     300
aactacgact ttactatgga ctactggggt caaggaacct cagtcacggt ctcctca        357
```

<210> SEQ ID NO 11
<211> LENGTH: 107
<212> TYPE: PRT
<213> ORGANISM: Mus musculus

<400> SEQUENCE: 11

```
Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ser
            20                  25                  30

Val Ala Trp Tyr Gln Gln Lys Pro Gly Gln Ser Pro Asn Leu Leu Ile
        35                  40                  45

Tyr Trp Ala Ser Ala Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105
```

<210> SEQ ID NO 12
<211> LENGTH: 321
<212> TYPE: DNA
<213> ORGANISM: Mus musculus

<400> SEQUENCE: 12

```
gacattgtga tgacccagtc tcacaaattc atgtccacat cagtaggaga cagggtcagc      60
atcatctgca aggccagtca ggatgtgggt acttctgtag cctggtatca acagaaacca     120
gggcaatctc ctaacctact gatttactgg gcatccgccc ggcacactgg agtccctgat     180
cgcttcacag gcagtggatc tgggacagat ttcactctca ccattagcaa tgtacagtct     240
gaagacttgg cagattattt ctgtcagcaa tatagcagtt atcctctcac gttcggtgct     300
gggaccaagc tggagctgaa a                                                321
```

<210> SEQ ID NO 13
<211> LENGTH: 17
<212> TYPE: PRT
<213> ORGANISM: Artificial Sequence
<220> FEATURE:
<223> OTHER INFORMATION: hu1217-1-1 HCDR2

```
<400> SEQUENCE: 13

Tyr Ile Thr Lys Gly Gly Gly Ser Thr Tyr Tyr Pro Asp Ser Val Lys
1               5                   10                  15

Gly

<210> SEQ ID NO 14
<211> LENGTH: 119
<212> TYPE: PRT
<213> ORGANISM: Artificial Sequence
<220> FEATURE:
<223> OTHER INFORMATION: hu1217-1-1 VH pro

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Tyr Met Tyr Trp Ile Arg Gln Ala Pro Gly Lys Gly Leu Glu Trp Val
        35                  40                  45

Ala Tyr Ile Thr Lys Gly Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Thr Asn Tyr Asp Phe Thr Met Asp Tyr Trp Gly Gln Gly
            100                 105                 110

Thr Leu Val Thr Val Ser Ser
        115

<210> SEQ ID NO 15
<211> LENGTH: 357
<212> TYPE: DNA
<213> ORGANISM: Artificial Sequence
<220> FEATURE:
<223> OTHER INFORMATION: hu1217-1-1 VH DNA

<400> SEQUENCE: 15
gaggtgcagc tggtggagag cggaggagga ctggtgcagc ctggaggcag cctgagactg      60
agctgcgcca ccagcggctt caccttctcc gactactaca tgtactggat caggcaggcc     120
cctggcaaag gcctggagtg ggtggcctac atcaccaagg gcggcggcag cacctactac     180
cccgatagcg tgaagggcag gttcaccatc agcagggaca cgccaagaa cacccctgtac    240 ctgcagatga acagcctgag ggccgaggat accgccgtgt actactgcgc caggcagacc     300
aactacgact tcaccatgga ctactggggc cagggcacac tggtgaccgt gagcagc       357

<210> SEQ ID NO 16
<211> LENGTH: 107
<212> TYPE: PRT
<213> ORGANISM: Artificial Sequence
<220> FEATURE:
<223> OTHER INFORMATION: hu1217-1-1 VK pro

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Gly Thr Ser
            20                  25                  30
```

```
Val Ala Trp Tyr Gln Gln Lys Pro Gly Gln Ala Pro Arg Leu Leu Ile
             35                  40                  45

Tyr Trp Ala Ser Ala Arg His Thr Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Ser Tyr Pro Leu
                 85                  90                  95

Thr Phe Gly Gly Gly Thr Lys Val Glu Ile Lys
            100                 105
```

<210> SEQ ID NO 17
<211> LENGTH: 321
<212> TYPE: DNA
<213> ORGANISM: Artificial Sequence
<220> FEATURE:
<223> OTHER INFORMATION: hu1217-1-1 VK DNA

<400> SEQUENCE: 17

```
gagatcgtga tgacccagag ccctgccaca ctgagcgtga gccctggcga gagagccacc    60
ctgagctgca aggccagcca ggatgtgggc accagcgtgg cctggtacca gcagaaaccc   120
ggccaggctc ccaggctgct gatctactgg gccagcgcca gacacacagg cgtgcctgcc   180
agatttagcg gcagcggcag cggcaccgag tttaccctga ccatcagcag cctgcagtcc   240
gaggacttcg ccgtgtacta ctgccagcag tacagcagct acccccctga cattcggcgg   300
ggcaccaagg tggagatcaa g                                             321
```

<210> SEQ ID NO 18
<211> LENGTH: 329
<212> TYPE: PRT
<213> ORGANISM: Artificial Sequence
<220> FEATURE:
<223> OTHER INFORMATION: IgG1mf

<400> SEQUENCE: 18

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Pro Ala Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175
```

Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Ala Leu Ala Ala Pro Ile Glu Lys Thr Ile Ser Lys Ala Lys Gly Gln
            210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
                275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 19
<211> LENGTH: 119
<212> TYPE: PRT
<213> ORGANISM: Artificial Sequence
<220> FEATURE:
<223> OTHER INFORMATION: hu1217-2-2 VH pro

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Thr Lys Gly Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Thr Asn Tyr Asp Phe Thr Met Asp Tyr Trp Gly Gln Gly
            100                 105                 110

Thr Leu Val Thr Val Ser Ser
        115

<210> SEQ ID NO 20
<211> LENGTH: 357
<212> TYPE: DNA
<213> ORGANISM: Artificial Sequence
<220> FEATURE:
<223> OTHER INFORMATION: hu1217-2-2 VH DNA

<400> SEQUENCE: 20
gaggtgcagc tggtggagag cggaggagga ctggtgcagc ctggaggcag cctgagactg    60
agctgcgccg ccagcggctt caccttctcc gactactaca tgtactgggt caggcaggcc   120

```
cctggcaaag gcctggagtg ggtggcctac atcaccaagg gcggcggcag cacctactac    180
cccgatagcg tgaagggcag gttcaccatc agcagggaca cgccaagaa cacccctgtac    240 ctgcagatga acagcctgag ggccgaggat accgccgtgt actactgcgc caggcagacc    300
aactacgact tcaccatgga ctactggggc cagggcacac tggtgaccgt gagcagc       357
```

<210> SEQ ID NO 21
<211> LENGTH: 107
<212> TYPE: PRT
<213> ORGANISM: Artificial Sequence
<220> FEATURE:
<223> OTHER INFORMATION: hu1217-2-2 VK pro

<400> SEQUENCE: 21

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Gly Thr Ser
            20                  25                  30

Val Ala Trp Tyr Gln Gln Lys Pro Gly Gln Ala Pro Arg Leu Leu Ile
        35                  40                  45

Tyr Trp Ala Ser Ala Arg His Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Leu
                85                  90                  95

Thr Phe Gly Gly Gly Thr Lys Val Glu Ile Lys
            100                 105
```

<210> SEQ ID NO 22
<211> LENGTH: 321
<212> TYPE: DNA
<213> ORGANISM: Artificial Sequence
<220> FEATURE:
<223> OTHER INFORMATION: hu1217-2-2 VK DNA

<400> SEQUENCE: 22

```
gagatcgtga tgacccagag ccctgccaca ctgagcgtga gccctggcga gagagccacc    60
ctgagctgca aggccagcca ggatgtgggc accagcgtgg cctggtacca gcagaaaccc    120
ggccaggctc ccaggctgct gatctactgg gccagcgcca gacacacagg catccctgcc    180
agatttagcg gcagcggcag cggcaccgag tttaccctga ccatcagcag cctgcagtcc    240
gaggacttcg ccgtgtacta ctgccagcag tacagcagct accccctgac attcggcggc    300
ggcaccaagg tggagatcaa g                                              321
```

<210> SEQ ID NO 23
<211> LENGTH: 119
<212> TYPE: PRT
<213> ORGANISM: Artificial Sequence
<220> FEATURE:
<223> OTHER INFORMATION: murinized 10A7 VH pro

<400> SEQUENCE: 23

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Thr Met His Trp Val Arg Gln Ala Pro Glu Lys Gly Leu Glu Trp Val
        35                  40                  45
```

```
Ala Tyr Ile Arg Ser Gly Ser Gly Ile Val Phe Tyr Ala Asp Thr Val
        50                  55                  60

Arg Gly Arg Phe Thr Ile Ser Arg Asp Asn Ala Lys Asn Thr Leu Phe
65              70                  75                  80

Leu Gln Met Thr Ser Leu Arg Ser Glu Asp Thr Ala Met Tyr Tyr Cys
            85                  90                  95

Ala Arg Arg Pro Leu Gly His Asn Thr Phe Asp Ser Trp Gly Gln Gly
            100                 105                 110

Thr Leu Val Thr Val Ser Ser
            115

<210> SEQ ID NO 24
<211> LENGTH: 113
<212> TYPE: PRT
<213> ORGANISM: Artificial Sequence
<220> FEATURE:
<223> OTHER INFORMATION: murinized 10A7 VK pro

<400> SEQUENCE: 24

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Ser Gly Val
    50                  55                  60

Pro Asp Arg Phe Thr Gly Ser Gly Ser Gly Thr Asp Phe Thr Leu Thr
65              70                  75                  80

Ile Ser Ser Val Gln Ala Glu Asp Leu Ala Val Tyr Tyr Cys Gln Gln
            85                  90                  95

Gly Ile Asn Asn Pro Leu Thr Phe Gly Gly Gly Thr Lys Leu Glu Ile
            100                 105                 110

Lys
```